(12) United States Patent
Coleman et al.

(10) Patent No.: US 8,030,495 B2
(45) Date of Patent: Oct. 4, 2011

(54) CYCLOPROPYL PYRROLIDINE OREXIN RECEPTOR ANTAGONISTS

(76) Inventors: Paul J. Coleman, Harleysville, PA (US); Swati P. Mercer, Philadelphia, PA (US); Anthony J. Roecker, North Wales, PA (US)

( * ) Notice: Subject to any disclaimer, the term of this patent is extended or adjusted under 35 U.S.C. 154(b) by 0 days.

(21) Appl. No.: 12/600,960

(22) PCT Filed: May 19, 2008

(86) PCT No.: PCT/US2008/006396
§ 371 (c)(1),
(2), (4) Date: Nov. 19, 2009

(87) PCT Pub. No.: WO2008/150364
PCT Pub. Date: Dec. 11, 2008

(65) Prior Publication Data
US 2010/0152191 A1    Jun. 17, 2010

Related U.S. Application Data

(60) Provisional application No. 60/931,459, filed on May 23, 2007.

(51) Int. Cl.
| C07D 277/62 | (2006.01) |
| C07D 261/20 | (2006.01) |
| C07D 263/54 | (2006.01) |
| C07D 249/04 | (2006.01) |
| C07D 401/14 | (2006.01) |
| C07D 473/02 | (2006.01) |
| C07D 241/36 | (2006.01) |
| C07D 471/02 | (2006.01) |
| C07D 413/14 | (2006.01) |
| A61K 31/50 | (2006.01) |
| A61K 31/501 | (2006.01) |
| A61K 31/4965 | (2006.01) |
| A61K 31/52 | (2006.01) |
| A61K 31/505 | (2006.01) |
| A61K 31/44 | (2006.01) |
| A61K 31/42 | (2006.01) |
| A61K 31/415 | (2006.01) |

(52) U.S. Cl. ........ 548/200; 548/222; 548/255; 544/284; 544/356; 544/265; 544/238; 546/115; 546/271.7; 514/249; 514/252.06; 514/255.05; 514/263.2; 514/275; 514/338; 514/367; 514/375; 514/395

(58) Field of Classification Search .................. None
See application file for complete search history.

(56) References Cited

U.S. PATENT DOCUMENTS

| 5,229,396 A | 7/1993 | Brighty |
| 6,927,200 B2 | 8/2005 | Bodet et al. |
| 7,582,659 B2 * | 9/2009 | Fukuda .................. 514/340 |
| 2004/0122017 A1 | 6/2004 | Chader et al. |
| 2010/0016401 A1 | 1/2010 | Aissaoui et al. |
| 2010/0204285 A1 | 8/2010 | Aissaoui et al. |

FOREIGN PATENT DOCUMENTS

| WO | WO 2004080463 A1 * | 9/2004 |
| WO | WO 2008/038251 | 4/2008 |
| WO | WO 2008/081399 | 7/2008 |
| WO | WO 2009/004584 | 1/2009 |
| WO | WO 2009/016560 | 2/2009 |
| WO | WO 2009/016564 | 2/2009 |

OTHER PUBLICATIONS

International Preliminary Report on Patentability for WO 2008/150364, (Nov. 24, 2009).
Coleman, et al., Expert Opin. Ther. Patents (2010), 20(3), 307-324.

* cited by examiner

*Primary Examiner* — Kamal Saeed
*Assistant Examiner* — Nyeemah A Grazier
(74) *Attorney, Agent, or Firm* — J. Eric Thies; Gerard M. Devlin

(57) ABSTRACT

The present invention is directed to cyclopropyl proline bis-amide compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

21 Claims, No Drawings

CYCLOPROPYL PYRROLIDINE OREXIN RECEPTOR ANTAGONISTS

CROSS REFERENCE TO RELATED APPLICATIONS

This application is a U.S. National Phase application under 35 U.S.C. §371 of PCT Application No. PCT/US2008/006396, filed May 19, 2008, which claims priority under 35 U.S.C. §119(e) from U.S. Ser. No. 60/931,459, filed May 23, 2007.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid hemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

Certain orexin receptor antagonists are disclosed in PCT patent publications WO 99/09024, WO 99/58533, WO 00/47576, WO 00/47577, WO 00/47580, WO 01/68609, WO 01/85693, WO 01/96302, WO 2002/044172, WO 2002/051232, WO 2002/051838, WO 2002/089800, WO 2002/090355, WO 2003/002559, WO 2003/002561, WO 2003/032991, WO 2003/037847, WO 2003/041711, WO 2003/051368, WO 2003/051872, WO 2003/051873, WO 2004/004733, WO 2004/026866, WO 2004/033418, WO 2004/041807, WO 2004/041816, WO 2004/052876, WO 2004/083218, WO 2004/085403, WO 2004/096780, WO 2005/060959, WO 2005/075458, WO 2005/118548, WO 2006/067224, WO 2006/110626, WO 2006/127550, WO 2007/019234, WO 2007/025069.

SUMMARY OF THE INVENTION

The present invention is directed to cyclopropyl pyrrolidine compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

DETAILED DESCRIPTION OF THE INVENTION

The present invention is directed to compounds of the formula I:

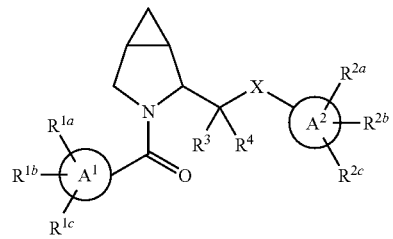

wherein:
$A^1$ is selected from the group consisting of phenyl, napthyl and heteroaryl;
$A^2$ is selected from the group consisting of phenyl, napthyl and heteroaryl;

X is selected from the group consisting of —NH—, —N($C_{1-6}$alkyl)-, —N($C_{1-6}$alkyl)-, —N($C_{3-6}$cycloalkyl)-, —O—, —S—, —S(O)—, —S(O)$_2$—, —CH$_2$—, —CH($C_{1-6}$alkyl)-, and —CH($C_{3-6}$cycloalkyl)-;

$R^{1a}$, $R^{1b}$ and $R^{1c}$ may be absent if the valency of $A^1$ does not permit such substitution and are independently selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—O$_n$-phenyl or —(C=O)$_m$—O$_n$-napthyl, where the phenyl or napthyl is unsubstituted or substituted with one or more substituents selected from $R^{13}$,
(8) —(C=O)$_m$—O$_n$-heterocycle, where the heterocycle is unsubstituted or substituted with one or more substituents selected from $R^{13}$,
(9) —(C=O)$_m$—NR$^{10}$R$^{11}$, wherein $R^{10}$ and $R^{11}$ are independently selected from the group consisting of:
 (a) hydrogen,
 (b) C$_{1-6}$alkyl, which is unsubstituted or substituted with $R^{13}$,
 (c) C$_{3-6}$alkenyl, which is unsubstituted or substituted with $R^{13}$,
 (d) C$_{3-6}$cycloalkyl which is unsubstituted or substituted with $R^{13}$,
 (e) phenyl, which is unsubstituted or substituted with $R^{13}$, and
 (f) heterocycle, which is unsubstituted or substituted with $R^{13}$,
(10) —S(O)$_2$—NR$^{10}$R$^{11}$,
(11) —S(O)$_q$—R$^{12}$, where q is 0, 1 or 2 and where $R^{12}$ is selected from the definitions of $R^{10}$ and $R^{11}$,
(12) —CO$_2$H,
(13) —CN, and
(14) —NO$_2$;

$R^{2a}$, $R^{2b}$ and $R^{2c}$ may be absent if the valency of $A^2$ does not permit such substitution and are independently selected from the group consisting of:
(1) hydrogen,
(2) halogen,
(3) hydroxyl,
(4) —(C=O)$_m$—O$_n$—C$_{1-6}$alkyl, where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-napthyl, where the phenyl or napthyl is unsubstituted or substituted with one or more substituents selected from $R^{13}$,
(9) —(C=O)$_m$—O$_n$-heterocycle, where the heterocycle is unsubstituted or substituted with one or more substituents selected from $R^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^3$ and $R^4$ are independently selected from the group consisting of:
(1) hydrogen,
(2) halogen,
(3) hydroxyl, and
(4) C$_{1-6}$alkyl, which is unsubstituted or substituted with one or more substituents selected from $R^{13}$,
or $R^4$ and $R^5$ may be joined together to form a C$_{3-6}$cycloalkyl with the carbon atom to which they are attached, where the cycloalkyl is unsubstituted or substituted with one or more substituents selected from $R^{13}$;

$R^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from $R^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from $R^{14}$,
(6) —(C=O)$_m$—C$_{2-4}$alkenyl, where the alkenyl is unsubstituted or substituted with one or more substituents selected from $R^{14}$,
(7) —(C=O)$_m$—C$_{2-4}$alkynyl, where the alkynyl is unsubstituted or substituted with one or more substituents selected from $R^{14}$,
(8) —(C=O)$_m$—O$_n$-phenyl or —(C=O)$_m$—O$_n$-napthyl, where the phenyl or napthyl is unsubstituted or substituted with one or more substituents selected from $R^{14}$,
(9) —(C=O)$_m$—O$_n$-heterocycle, where the heterocycle is unsubstituted or substituted with one or more substituents selected from $R^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;

or a pharmaceutically acceptable salt thereof.

An embodiment of the present invention includes compounds of the formula Ia:

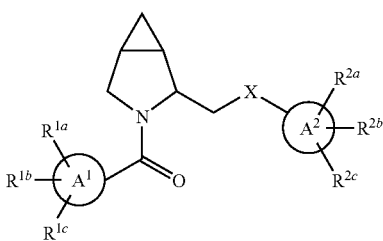

wherein X, A$^1$, A$^2$, R$^{1a}$, R$^{1b}$, R$^{1c}$, R$^{2a}$, R$^{2b}$ and R$^{2c}$ are defined herein; or a pharmaceutically acceptable salt thereof.

An embodiment of the present invention includes compounds of the formula Ib:

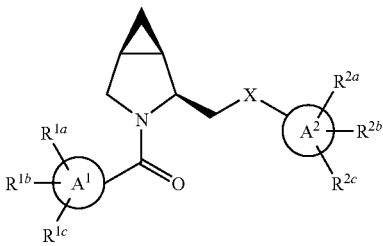

wherein X, A$^1$, A$^2$, R$^{1a}$, R$^{1b}$, R$^{1c}$, R$^{2a}$, R$^{2b}$ and R$^{2c}$ are defined herein; or a pharmaceutically acceptable salt thereof.

An embodiment of the present invention includes compounds of the formula Ic:

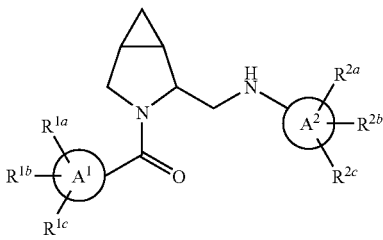

wherein X, A$^1$, A$^2$, R$^{1a}$, R$^{1b}$, R$^{1c}$, R$^{2a}$, R$^{2b}$ and R$^{2c}$ are defined herein; or a pharmaceutically acceptable salt thereof.

An embodiment of the present invention includes compounds of the formula Id:

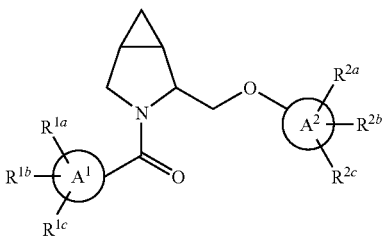

wherein X, A$^1$, A$^2$, R$^{1a}$, R$^{1b}$, R$^{1c}$, R$^{2a}$, R$^{2b}$ and R$^{2c}$ are defined herein; or a pharmaceutically acceptable salt thereof.

An embodiment of the present invention includes compounds of the formula Ie:

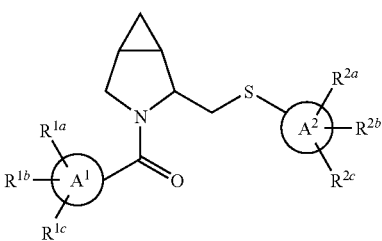

wherein X, A$^1$, A$^2$, R$^{1a}$, R$^{1b}$, R$^{1c}$, R$^{2a}$, R$^{2b}$ and R$^{2c}$ are defined herein; or a pharmaceutically acceptable salt thereof.

An embodiment of the present invention includes compounds wherein X is —S. An embodiment of the present invention includes compounds wherein X is —NH—. An embodiment of the present invention includes compounds wherein X is —O—.

An embodiment of the present invention includes compounds wherein A$^1$ is selected from the group consisting of phenyl, pyrazolyl, pyridyl and thiazolyl.

An embodiment of the present invention includes compounds wherein A$^1$ is selected from the group consisting of benzimidazole, N-methylbenzimidazole, benzthiazole and benzoxazole.

An embodiment of the present invention includes compounds wherein A$^1$ is benzimidazole, R$^{1a}$ is hydrogen or C$_{1-6}$alkyl, R$^{1b}$ is hydrogen and R$^{1c}$ is hydrogen.

An embodiment of the present invention includes compounds wherein R$^{1a}$, R$^{1b}$ and R$^{1c}$ are independently selected from the group consisting of:
(1) hydrogen,
(2) halogen,
(3) hydroxyl,
(4) C$_{1-6}$alkyl, which is unsubstituted or substituted with halogen, hydroxyl, phenyl or napthyl,
(5) —O—C$_{1-6}$alkyl, which is unsubstituted or substituted with halogen, hydroxyl or phenyl,
(6) heteroaryl, wherein heteroaryl is selected from pyrrolyl, imidazolyl, indolyl, pyridyl, and pyrimidinyl, which is unsubstituted or substituted with halogen, hydroxyl, C$_{1-6}$alkyl, —O—C$_{1-6}$alkyl or —NO$_2$,
(7) phenyl, which is unsubstituted or substituted with halogen, hydroxyl, C$_{1-6}$alkyl, —O—C$_{1-6}$alkyl or —NO$_2$,
(8) —O-phenyl, which is unsubstituted or substituted with halogen, hydroxyl, C$_{1-6}$alkyl, —O—C$_{1-6}$alkyl or —NO$_2$, and
(9) —NH—C$_{1-6}$alkyl, or —N(C$_{1-6}$alkyl)(C$_{1-6}$alkyl), which is unsubstituted or substituted with halogen, hydroxyl, C$_{1-6}$alkyl, —O—C$_{1-6}$alkyl or —NO$_2$.

An embodiment of the present invention includes compounds wherein R$^{1a}$, R$^{1b}$ and R$^{1c}$ are independently selected from the group consisting of:
(1) hydrogen,
(2) halogen,
(3) hydroxyl,
(4) C$_{1-6}$alkyl, which is unsubstituted or substituted with halogen, hydroxyl or phenyl or napthyl, and
(5) —O—C$_{1-6}$alkyl, which is unsubstituted or substituted with halogen, hydroxyl or phenyl.

An embodiment of the present invention includes compounds wherein $R^{1a}$, $R^{1b}$ and $R^{1c}$ are independently selected from the group consisting of:
(1) hydrogen,
(2) halogen, and
(3) $C_{1-6}$alkyl.

An embodiment of the present invention includes compounds wherein $R^{1a}$, $R^{1b}$ and $R^{1c}$ are independently selected from the group consisting of:
(1) hydrogen,
(2) chloro,
(3) fluoro, and
(4) methyl.

An embodiment of the present invention includes compounds wherein $A^2$ is benzimidazolyl, benzoxazolyl, benzthiazolyl, pyrimidinyl, quinazolinyl or quinoxazolinyl which is substituted with $R^{2a}$, $R^{2b}$ and $R^{2c}$.

An embodiment of the present invention includes compounds wherein $A^2$ is phenyl or pyridyl which is substituted with $R^{2a}$, $R^{2b}$ and $R^{2c}$.

An embodiment of the present invention includes compounds wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl or napthyl,
(5) —O—$C_{1-6}$alkyl, which is unsubstituted or substituted with halogen, hydroxyl or phenyl,
(6) heteroaryl, wherein heteroaryl is selected from pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —$NO_2$,
(7) phenyl, which is unsubstituted or substituted with halogen, hydroxyl, $C_{1-6}$alkyl, —O—$C_{1-6}$alkyl or —$NO_2$,
(8) —O-phenyl, which is unsubstituted or substituted with halogen, hydroxyl, $C_{1-6}$alkyl, or —$NO_2$, and
(9) —NH—$C_{1-6}$alkyl, or —N($C_{1-6}$alkyl)($C_{1-6}$alkyl), which is unsubstituted or substituted with halogen, hydroxyl, $C_{1-6}$alkyl, —O—$C_{1-6}$alkyl or —$NO_2$.

An embodiment of the present invention includes compounds wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl, and
(6) —NH—$C_{1-6}$alkyl, or —N($C_{1-6}$alkyl)($C_{1-6}$alkyl), which is unsubstituted or substituted with halogen.

An embodiment of the present invention includes compounds wherein $R^{2a}$, $R^{2b}$ and $R^{2c}$ are independently selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen, and
(5) —NH—$C_{1-6}$alkyl, or —N($C_{1-6}$alkyl)($C_{1-6}$alkyl), which is unsubstituted or substituted with halogen.

An embodiment of the present invention includes compounds wherein $R^{2a}$, $R^{2b}$ and $R^{2c}$ are independently selected from the group consisting of:
(1) hydrogen,
(2) chloro,
(3) fluoro,
(4) bromo,
(5) methoxy,
(6) t-butoxy,
(7) difluoromethyl, and
(8) trifluoromethyl,
(9) —N($CH_3$).

An embodiment of the present invention includes compounds wherein $R^{2b}$ is hydrogen, $R^{2c}$ is hydrogen and $R^{2a}$ is selected from the group consisting of:
(1) 2-phenyl,
(2) 2-pyrrole, and
(3) 2-(3-pyridyl).

An embodiment of the present invention includes compounds wherein $A^2$ is phenyl which is substituted with pyrrolyl.

An embodiment of the present invention includes compounds wherein $R^3$ is hydrogen or $C_{1-6}$alkyl. An embodiment of the present invention includes compounds wherein $R^3$ is hydrogen or methyl. An embodiment of the present invention includes compounds wherein $R^3$ is hydrogen. An embodiment of the present invention includes compounds wherein $R^4$ is hydrogen or $C_{1-6}$alkyl. An embodiment of the present invention includes compounds wherein $R^4$ is hydrogen or methyl. An embodiment of the present invention includes compounds wherein $R^4$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% $CO_2$) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. The intrinsic orexin receptor antagonist activity of a compound which may be used in the present invention may be determined by these assays.

In particular, the compounds of the following examples had activity in antagonizing the rat orexin-1 receptor and/or the human orexin-2 receptor in the aforementioned assays, generally with an $IC_{50}$ of less than about 50 μM. Many of compounds within the present invention had activity in antagonizing the rat orexin-1 receptor and/or the human orexin-2 receptor in the aforementioned assays with an $IC_{50}$ of less than about 100 nM. Such a result is indicative of the intrinsic activity of the compounds in use as antagonists of orexin-1 receptor and/or the orexin-2 receptor. The present invention also includes compounds within the generic scope of the invention which possess activity as agonists of the orexin-1 receptor and/or the orexin-2 receptor. With respect to other pyrrolidine compounds, the present compounds exhibit unexpected properties, such as with respect to increased oral bioavailability, metabolic stability, and/or selectivity with respect to other receptors.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reducation of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD); GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulinotropin); and GLP-1 (7-36)—NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo; (g) PPARδ agonists; (h) PPAR α/δ agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11, Phe13, Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptideYY, PYY 3-36, peptideYY analogs, derivatives, and fragments such as BIM-43073D, BIM-43004C (Olitvak, D. A. et al., Dig. Dis. Sci. 44(3):643-48 (1999)); (51) NeuropeptideY2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) NeuropeptideY4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitor such as BVT 3498, BVT 2733; (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; MTBE: methyl tert-butyl ether; $SOCl_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

REACTION SCHEME A

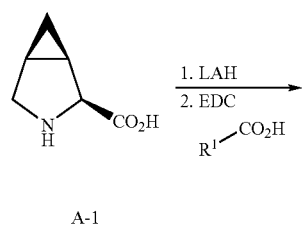

A-1

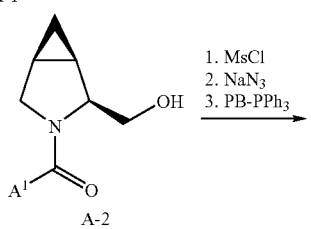

A-2

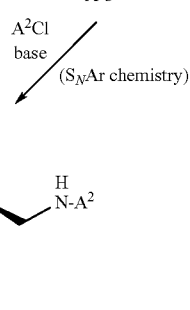

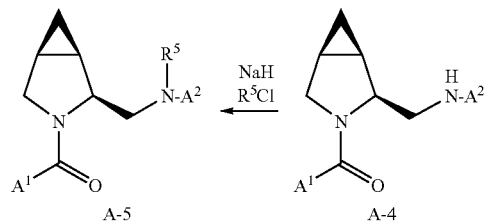

A-5     A-4

(1R,2S,5S)-3-azabicyclo[3.1.0]hexane-2-carboxylic acid (A-1) is reduced and selectively coupled to carboxylic acids to afford A-2. The alcohol of A-2 is transformed to an amine (A-3) via mesylation, azide displacement and reduction by triphenylphosphine. The resulting amine is then functionalized with various heterocycles via $S_NAr$ chemistry to afford A-4. The secondary amines are further reacted with strong based (i.e. sodium hydride) and capped with electrophiles to afford A-5.

REACTION SCHEME B

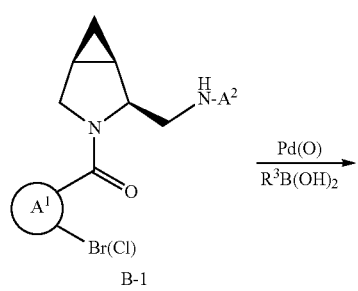

B-1

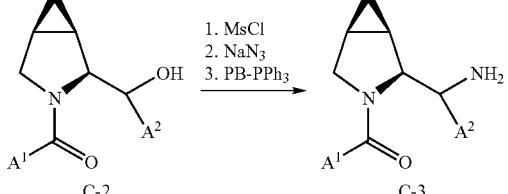

B-2

Compounds of formula B-1 are transformed to B-2 via Suzuki coupling with various boronic acids.

REACTION SCHEME C

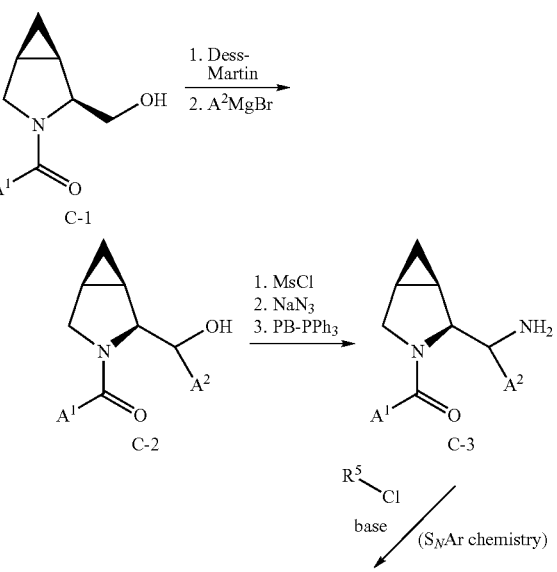

The alcohol moiety in C-1 is oxidized with Dess-Martin periodinane and subsequently reacted with Grignard reagents to afford C-2. The alcohol is then be converted to an amine via mesylation, azide displacement and reduction to afford C-3. Finally, the amine of C-3 is reacted under $S_NAr$ chemistry to afford C4.

REACTION SCHEME D

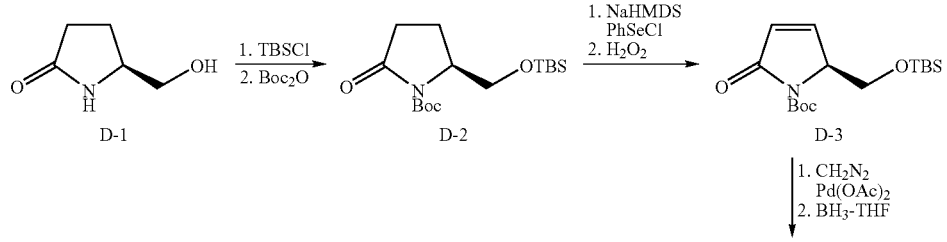

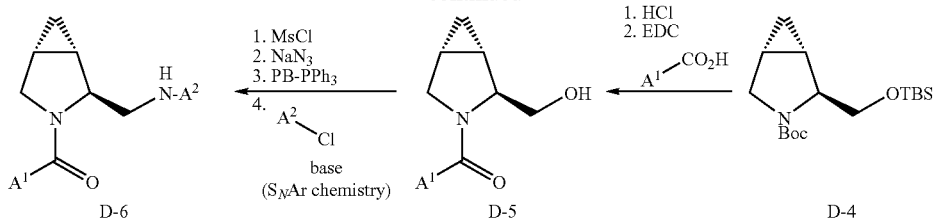

(5S)-5-(hydroxymethyl)pyrrolidin-2-one (D-1) is protected by treatment with TBSCl followed by $Boc_2O$ to afford D-2. This compound is unsaturated via alpha-selenation and elimination with hydrogen peroxide to afford D-3. Diastereoselective cyclopropanation using Pd(OAc)2 and diazomethane followed by amide reduction affords D-4. Deprotection of D-4 and coupling with various carboxylic acids provides compounds of type D-5. The alcohol is transformed to an amine via mesylation, azide displacement and reduction. Finally, the amine is reacted under $S_NAr$ chemistry to afford D-6.

REACTION SCHEME E

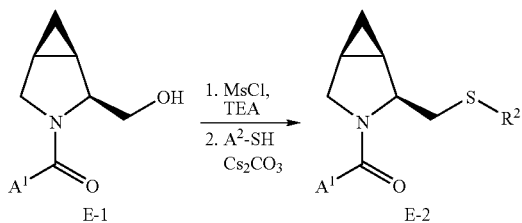

Alcohols of type E-1 are transformed to E-2 via mesylation and displacement with various thiols.

REACTION SCHEME F

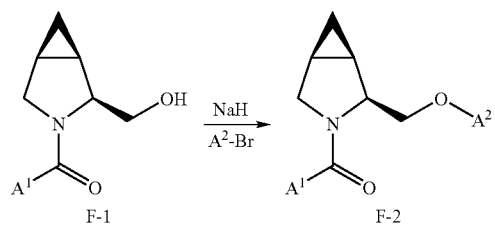

Alcohols of type F-1 are alkylated under the action of strong base (i.e. sodium hydride) and reaction with various electrophiles to yield F-2.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1

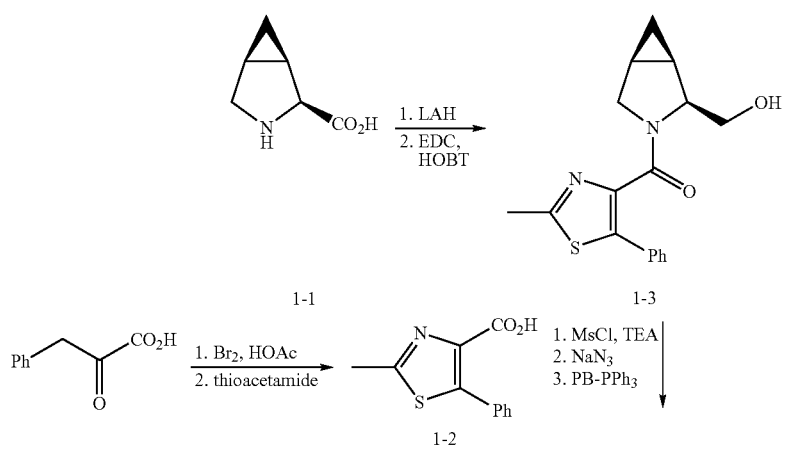

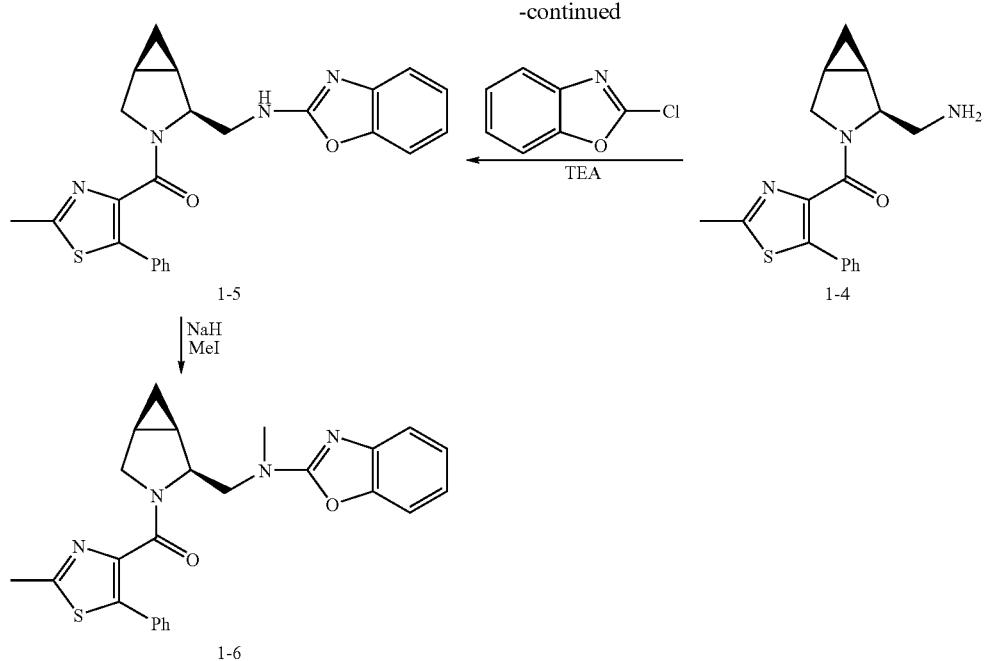

2-methyl-5-phenyl-1,3-thiazole-4-carboxylic acid (1-2)

To a solution of phenylpyruvic acid (25.0 g, 152.3 mmol) in glacial acetic acid (300 mL) was added bromine (24.4 g, 152.3 mmol) dropwise over 5 minutes. The reaction was concentrated directly and the mixture was azeotroped with hexanes. The resulting orange solid was used without further purification in the subsequent reaction. The orange solid and thioacetamide were dissolved in ethanol (350 mL) and the reaction was heated to reflux for 30 minutes. After cooling to room temperature the reaction was treated with concentrated ammonium hydroxide until pH 10 was reached and a precipitate formed. The precipitate was filtered and dissolved in water with heating to 45° C. This solution was triturated with 1N HCl until pH 3 was reached and a solid crashed out of solution. The mixture was cooled in an ice bath and filtered to afford a white solid (1-2) after drying overnight under high vacuum. $^1$H NMR (500 MHz, CD$_3$OD) δ 7.53-7.48 (m, 2H), 7.43-7.38 (m, 3H), 2.71 (s, 3H). ESI+ MS: [M+H]$^+$ 220.0.

{(1R,2S,5S)-3-[(2-methyl-5-phenyl-1,3-thiazol-4-yl)carbonyl]-3-azabicyclo[3.1.0]hex-2-yl}methanol (1-3, racemic)

To a solution of cis-3-azabicyclo[3.1.0]hexane-2-carboxylic acid (1.0 g, 7.9 mmol) in THF (30 mL) at ambient temperature was added LAH (0.73 g, 19.1 mmol) with gas evolution. The reaction was stirred 6 hours and quenched with water (3 mL total) and 1M NaOH (1.5 mL). The mixture was diluted with EtOAc (100 mL) and dried over magnesium sulfate. The reaction mixture was concentrated and the resulting oil was used without further purification. To a solution of crude aminoalcohol (0.26 g, 2.28 mmol) and 2-methyl-5-phenyl-1,3-thiazole-4-carboxylic acid (1-2, 0.50 g, 2.28 mmol) in CH$_2$Cl$_2$ (11 mL) was added EDC (0.53 g, 2.74 mmol), HOBT (0.42 g, 2.74 mmol), triethylamine (0.28 g, 2.74 mmol) and the reaction was stirred overnight at ambient temperature for 12 hours. The reaction was quenched with water (5 mL) and saturated sodium bicarbonate (5 mL) and diluted with EtOAc (20 mL). The organic phase was washed several times with water (3×10 mL), dried organics over magnesium sulfate and concentrated. The residue was purified by normal phase silica gel chromatography (0 to 100% EtOAc in hexanes, then 0 to 20% MeOH in EtOAc) to afford the product (1-3) as an oil. ESI+ MS: [M+H]$^+$ 315.2.

({(1R,2S,5S)-3-[(2-methyl-5-phenyl-1,3-thiazol-4-yl)carbonyl]-3-azabicyclo[3.1.0]hex-2-yl}methyl) amine (1-4, racemic)

To a solution of 1-3 (0.30 g, 0.95 mmol) in CH$_2$Cl$_2$ (5 mL) at ambient temperature was added triethylamine (0.19 g, 1.9 mmol) and methanesulfonyl chloride (0.16 g, 1.43 mmol) and the reaction was stirred for 0.5 hours. The reaction was quenched with water (5 mL) and the reaction was extracted with CH$_2$Cl$_2$ (20 mL). The organic phase was dried over magnesium sulfate and concentrated to afford an oil which was used without further purification. The residue was redissolved in DMF (5 mL) and to this solution was added sodium azide (0.31 g, 4.77 mmol) and the reaction was heated to 60° C. for 1 h. The reaction was cooled and diluted with EtOAc (25 mL). The organic phase was washed with water (3×20 mL), dried over magnesium sulfate and concentrated to an oil which was used without further purification. The residue was redissolved in THF (5 mL) at ambient temperature and to the solution was added polymer-bound triphenylphosphine (1 g, 2.2 mmol; 2.2 mmol/g loading) and water (0.085 g, 4.75 mmol). The reaction was stirred for 12 hours and quenched with magnesium sulfate. The reaction was filtered to yield 1-4 as an oil of >90% purity ESI+ MS: [M+H]$^+$ 314.0.

N-({(1R,2S,5S)-3-[(2-methyl-5-phenyl-1,3-thiazol-4-yl)carbonyl]-3-azabicyclo[3.1.0]hex-2-yl}methyl)-1,3-benzoxazol-2-amine (1-5, racemic)

To a solution of 1-4 (0.050 g, 0.16 mmol) in DMF (0.53 mL) at ambient temperature was added triethylamine (0.04 g, 0.40 mmol) and 2-chlorobenzoxazole (0.034 g, 0.22 mmol) and the reaction was heated for 3 hours at 65° C. The reaction was cooled and quenched with water (10 mL) and diluted with EtOAc (20 mL). The organic phases were washed with water (3×10 mL) and dried over magnesium sulfate. The residue was purified by normal phase silica gel chromatography (0 to 100% EtOAc in hexanes, then 0 to 20% MeOH in EtOAc) to afford the product (1-5) as a foamy, off-white solid. $^1$H NMR (500 MHz, CDCl$_3$) δ 7.46-7.33 (m, 5H), 7.30-7.25 (m, 1H), 7.23 (d, J=8.0 Hz, 1H), 7.15 (t, J=7.5 Hz, 1H), 7.01 (t, J=7.5 Hz, 1H), 4.35-4.33 (m, 1H), 4.09-4.06 (m, 1H), 3.53-3.44 (m, 2H), 3.25 (d, J=10.5 Hz, 1H), 2.72 (s, 3H), 1.86-1.83 (m, 1H), 1.39-1.35 (m, 1H), 0.57-0.53 (m, 1H), 0.12-0.09 (m, 1H). HRMS [M+H] C$_{24}$H$_{22}$N$_4$O$_2$S$_1$ calc'd 431.1536, found 431.1543. This compound was separated into its pure enantiomers by chiral HPLC under the following conditions: Chiracel OD column (2×25 cm), 8 mL/min flow rate, 70/30 hexanes/iPrOH with 1% diethylamine as a modifier. The pure enantiomers eluted under these conditions to give enantiomer 1: retention time=23.9 min (more active) and enantiomer 2: retention time=41.8 min (less active).

N-methyl-N-({(1R,2S,5S)-3-[(2-methyl-5-phenyl-1,3-thiazol-4-yl)carbonyl]-3-azabicyclo[3.1.0]hex-2-yl}methyl)-1,3-benzoxazol-2-amine (1-6, racemic)

To a solution of 1-5 (0.10 g, 0.23 mmol) in THF (1.1 mL) at ambient temperature was added sodium hydride (0.019 g, 0.47 mmol, 60% dispersion in mineral oil) and iodomethane (0.099 g, 0.70 mmol) and the reaction was stirred for 0.5 hours. The reaction was quenched with water (10 mL) and diluted with EtOAc (20 mL). The organic phases were washed with water (3×10 mL) and dried over magnesium sulfate. The residue was purified by normal phase silica gel chromatography (0 to 100% EtOAc in hexanes) to afford the product (1-6) as a foamy, off-white solid. $^1$H NMR (500 MHz, CDCl$_3$) δ 7.50-7.33 (m, 6H), 7.26 (d, J=8.0 Hz, 1H), 7.15 (t, J=7.5 Hz, 1H), 7.00 (t, J=7.5 Hz, 1H), 4.54-4.43 (m, 2H), 3.65-3.59 (m, 1H), 3.45-3.42 (m, 1H), 3.34 (s, 3H), 3.25 (d, J=10.0 Hz, 1H), 2.72 (s, 3H), 1.70-1.63 (m, 1H), 1.50-1.43 (m, 1H), 0.57-0.53 (m, 1H), 0.22-0.19 (m, 1H). HRMS [M+H] C$_{25}$H$_{24}$N$_4$O$_2$S$_1$ calc'd 445.1693, found 445.1698. This compound was separated into its pure enantiomers by chiral HPLC under the following conditions: Chiracel OD column (2×25 cm), 8 mL/min flow rate, 70/30 hexanes/EtOH. The pure enantiomers eluted under these conditions to give enantiomer 1: retention time=7.2 min (more active) and enantiomer 2: retention time=10.4 min (less active).

EXAMPLE 2

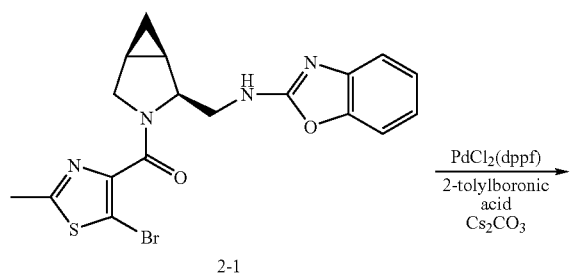

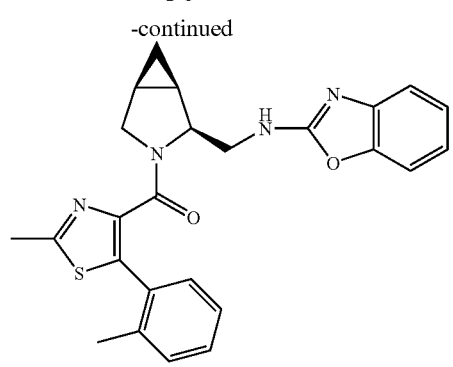

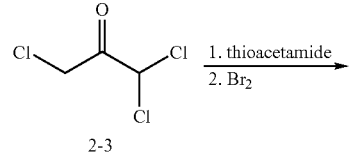

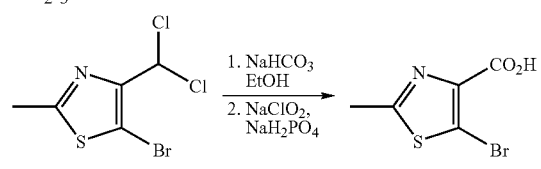

N-[((1R,2S,5S)-3-{[2-methyl-5-(2-methylphenyl)-1,3-thiazol-4-yl]carbonyl}-3-azabicyclo[3.1.0]hex-2-yl)methyl]-1,3-benzoxazol-2-amine (2-2)

To a solution of N-({(1R,2S,5S)-3-[(5-bromo-2-methyl-1,3-thiazol-4-yl)carbonyl]-3-azabicyclo[3.1.0]hex-2-yl}methyl)-1,3-benzoxazol-2-amine (0.010 g, 0.023 mmol) and 2-tolylboronic acid (0.012 g, 0.092 mmol) in DMF (0.25 mL) was added 1M aqueous cesium carbonate (0.092 mL, 0.092 mmol) and PdCl$_2$(dppf) (0.0016 g, 0.0023 mmol) and heated in a microwave to 130° C. for 10 minutes. The system was cooled to room temperature, extracted with EtOAc, washed with water, dried over sodium sulfate and concentrated. The crude reaction mixture was then purified using reverse phase conditions (5%→60% 0.1% TFA in water: 0.1% TFA in acetonitrile) followed by free basing with saturated sodium carbonate to afford the title compound (2-2) as a bone powder. $^1$H NMR (500 MHz, CDCl$_3$) δ 7.35 (m, 1H), 7.19-7.34 (m, 5H), 7.14 (m, 1H), 7.02 (m, 1H), 4.29 (m, 1H), 3.98 (m, 1H), 3.52 (m, 2H), 3.39 (m, 1H), 2.75 (s, 3H), 2.32 (s, 3H), 1.81 (m, 1H), 1.44 (m, 1H), 0.882 (m, 1H), 0.548 (m, 1H). HRMS [M+H] C$_{25}$H$_{24}$N$_4$O$_2$S$_1$ calc'd 445.1693, found 445.1679.

5-bromo-4-(dichloromethyl)-2-methyl-1,3-thiazole (2-4)

To a solution of 1,1,3-trichloroacetone (30.0 g, 185.85 mmol) in acetone (80.0 mL) was added thioacetamide (18.15 g, 241.60 mmol) and stirred at room temperature overnight. The mixture was then concentrated and re-dissolved in concentrated HCl (30.0 mL) and stirred initially at room temperature for 1 h followed by heating to 55° C. for 70 h. The system was cooled to room temperature, poured into ice water, extracted with EtOAc, dried over sodium sulfate and concentrated. The crude reaction mixture was purified using normal phase conditions (0%→20% EtOAc: hexanes) to afford a pale yellow solid. To this solid (13.9 g, 76.0 mmol) in acetic acid (109 mL) was added bromine (5.90 mL, 115 mmol) and the system was stirred at room temperature overnight. The mixture was poured into ice water, extracted with EtOAc, dried over sodium sulfate and concentrated. The crude reaction mixture was purified using normal phase conditions (5% EtOAc:hexanes) to afford the title compound (2-4) as a bone powder. ESI+ MS: 261.9 [M+H]+.

5-bromo-2-methyl-1,3-thiazole-4-carboxylic acid (2-5)

To a solution of 5-bromo-4-(dichloromethyl)-2-methyl-1,3-thiazole (7.58 g, 29.0 mmol) in ethanol (180.0 mL) was added saturated aqueous sodium bicarbonate (60.0 mL) and the system was stirred at 80° C. overnight. The mixture was then cooled to room temperature, diluted with EtOAc, extracted with water, dried over sodium sulfate and concentrated. The crude reaction mixture was purified using normal phase conditions (0%→÷30% EtOAc: hexanes) to afford a mixture of the desired compound and an acetal byproduct. This mixture was then treated with 1N HCl (12.25 mL, 12.25 mmol) for 0.5 h at room temperature followed by neutralization with 2N NaOH to a pH of 7.0. Extraction with EtOAc and water afforded the product as a pale yellow crystalline solid. To this solid (5.0 g, 24.26 mmol) in THF/t-BuOH/Water (40 mL/80 mL/20 mL) was added sodium phosphate (17.22 g, 121.0 mmol), 2-methyl-2-butene (64.0 mL, 607 mmol) and sodium chlorite (5.49 g, 60.7 mmol) and was stirred at room temperature for 1 h. The system was then acidified with 1N HCl to a pH of 3.0, extracted with EtOAc, washed with water, dried over sodium sulfate and concentrated. Removal of solvent in vacuo afforded the title compound (2-5) as a powder. 1H NMR (500 MHz, CDCl3) δ 2.72 (s, 3H). ESI+ MS: 222.8 [M+H]+.

EXAMPLE 3

(1S)-1-{(1R,2S,5S)-3-[(2-methyl-5-phenyl-1,3-thiazol-4-yl)carbonyl-3-azabicyclo[3.1.0]hex-2-yl}ethanol (3-1, racemic)

To a solution of 1-3 (0.9 g, 2.9 mmol) in CH2Cl2 (15 mL) at ambient temperature was added NaHCO3 (0.96 g, 11.4 mmol) and Dess-Martin periodinane (1.6 g, 3.7 mmol). The reaction was stirred 3 hours and quenched with water (20 mL) and saturated NaHCO3 (15 mL). The reaction was diluted with EtOAc (100 mL) and washed with saturated NaHCO3 (4×25 mL) and brine (1×50 mL). The reaction mixture was dried over magnesium sulfate, concentrated, and the resulting oil was used without further purification. To a solution of crude aldehyde (0.44 g, 1.41 mmol) in THF (3 mL) at 0° C. was added a solution of methylmagnesium bromide in THF (0.94 mL, 2.82 mmol, 3M in THF and the reaction was stirred for 1 hour. The reaction was quenched with saturated NH4Cl (5 mL) and diluted with EtOAc (20 mL). The organic phase was washed several times with water (3×10 mL) and the combined organic phase was dried over magnesium sulfate and concentrated. The residue (3-1, oil) was used without further purification. ESI+ MS: [M+H]+ 329.2.

((1S)-1-{(1R,2S,5S)-3-[(2-methyl-5-phenyl-1,3-thiazol-4-yl)carbonyl]-3-azabicyclo[3.1.0]hex-2-yl}ethyl)amine (3-2, racemic)

To a solution of 3-1 (0.46 g, 1.41 mmol) in CH2Cl2 (5 mL) at ambient temperature was added triethylamine (0.36 g, 3.52 mmol) and methanesulfonyl chloride (0.24 g, 2.11 mmol) and the reaction was stirred for 0.5 hours. The reaction was quenched with water (5 mL) and the reaction was extracted with CH2Cl2 (20 mL). The organic phase was dried over magnesium sulfate and concentrated to afford an oil which was used without further purification. The residue was redissolved in DMF (5 mL) and to this solution was added sodium azide (0.92 g, 14.1 mmol) and the reaction was heated to 65° C. for 1 h. The reaction was cooled and diluted with EtOAc

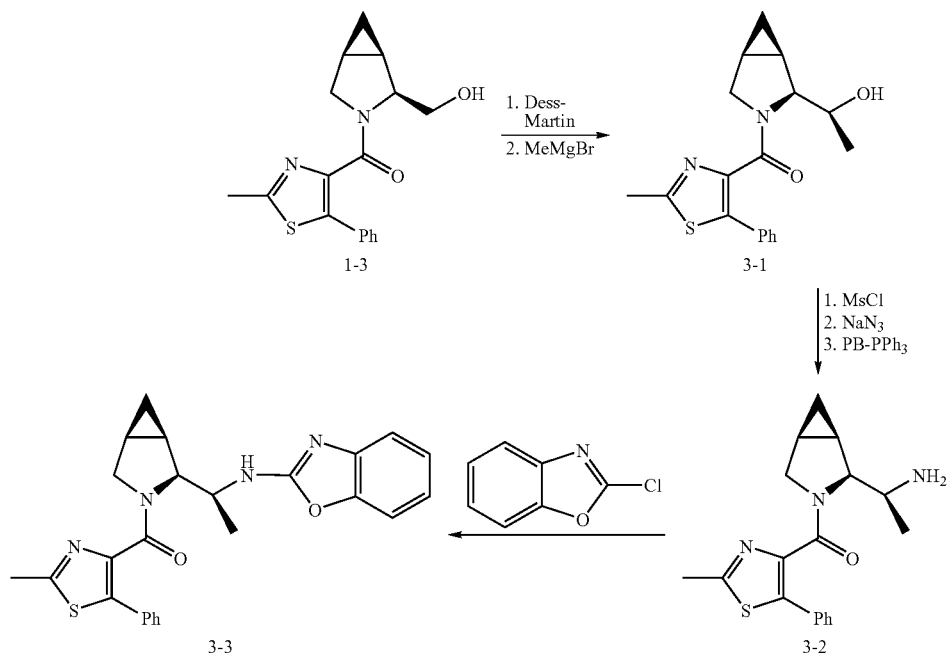

(25 mL). The organic phase was washed with water (3×20 mL), dried over magnesium sulfate and concentrated to an oil which was used without further purification. The residue was redissolved in THF (5 mL) at ambient temperature and to the solution was added polymer-bound triphenylphosphine (1.1 g, 2.4 mmol; 2.2 mmol/g loading) and water (0.25 g, 14.1 mmol). The reaction was stirred for 12 hours and quenched with magnesium sulfate. The reaction was filtered to yield 3-2 as an oil of >90% purity. ESI+ MS: [M+H]$^+$ 328.2.

N-((1S)-1-{(1R,2S,5S)-3-[(2-methyl-5-phenyl-1,3-thiazol-4-yl)carbonyl]-3-azabicyclo[3.1.0]hex-2-yl}ethyl)-1,3-benzoxazol-2-amine (3-3, racemic)

To a solution of 3-2 (0.030 g, 0.09 mmol) in DMF (0.53 mL) at ambient temperature was added triethylamine (0.028 g, 0.28 mmol) and 2-chlorobenzoxazole (0.020 g, 0.13 mmol) and the reaction was heated for 3 hours at 50° C. The reaction was cooled and quenched with water (10 mL) and diluted with EtOAc (20 mL). The organic phases were washed with water (3×10 mL) and dried over magnesium sulfate. The residue was purified by normal phase silica gel chromatography (0 to 100% EtOAc in hexanes) to afford the 3-3 as a foamy, off-white solid. $^1$H NMR (500 MHz, CDCl$_3$) δ 7.67-7.63 (m, 1H), 7.42 (d, J=7.5 Hz, 1H), 7.28 (d, J=8.0 Hz, 2H), 7.21-7.12 (m, 3H), 7.06-6.98 (m, 2H), 4.77-4.72 (m, 1H), 3.72-3.59 (m, 2H), 2.85 (d, J=11.5 Hz, 1H), 2.71 (s, 3H), 1.90-1.83 (m, 1H), 1.68-1.60 (m, 1H), 1.47 (d, J=6.0 Hz, 3H), 0.79-0.73 (m, 1H), 0.39-0.36 (m, 1H). HRMS [M+H] C$_{25}$H$_{24}$N$_4$O$_2$S$_1$ calc'd 445.1674, found 445.1693.

EXAMPLE 4 resuspended in acetonitrile (200 mL) and to the solution was added 4-DMAP (5.2 g, 42.1 mmol) and Boc$_2$O (9.6 g, 44.1 mmol) The reaction was stirred at ambient temperature for 12 h and quenched with water (200 mL). The reaction was diluted with EtOAc (500 mL) and subsequently washed with water (200 mL) and brine (200 mL). The combined organic phase was dried over magnesium sulfate and concentrated. The residue was purified by normal phase silica gel chromatography (0 to 65% EtOAc in hexanes) to afford the product (4-2) as an oil.

tert-butyl (2S)-2-({[tert-butyl(dimethyl)silyl]oxy}methyl)-5-oxo-2,5-dihydro-1H-pyrrole-1-carboxylate (4-3)

To a solution of NaHMDS (35 mL, 35 mmol, 1.0M solution in THF) in THF (45 mL) at 0° C. was added DMPU (4.8 mL) and the reaction mixture was stirred 20 minutes. The reaction mixture was cooled to −78° C. and to it was added a solution of 4-2 (4.8 g, 14.6 mmol) in THF (20 mL) and the reaction was stirred an additional 30 minutes. At this time a solution of phenylselenenyl chloride (3.35 g, 17.5 mmol) in THF (15 mL) was added and the reaction was stirred at −78° C. for 2 h. The reaction quenched with saturated NH$_4$Cl (200 mL) at −78° C. and the reaction mixture was warmed to ambient temperature. The reaction mixture was extracted with EtOAc (3×200 mL) and the combined organic phase was dried over magnesium sulfate and concentrated. The residue was resuspended in THF (100 mL) and cooled to 0° C. To the reaction mixture was added H$_2$O$_2$ (6.4 mL, 73 mmol, 35% solution in water). The reaction mixture was stirred 2 h and quenched with saturated NaHCO$_3$ (200 mL). The reaction was extracted

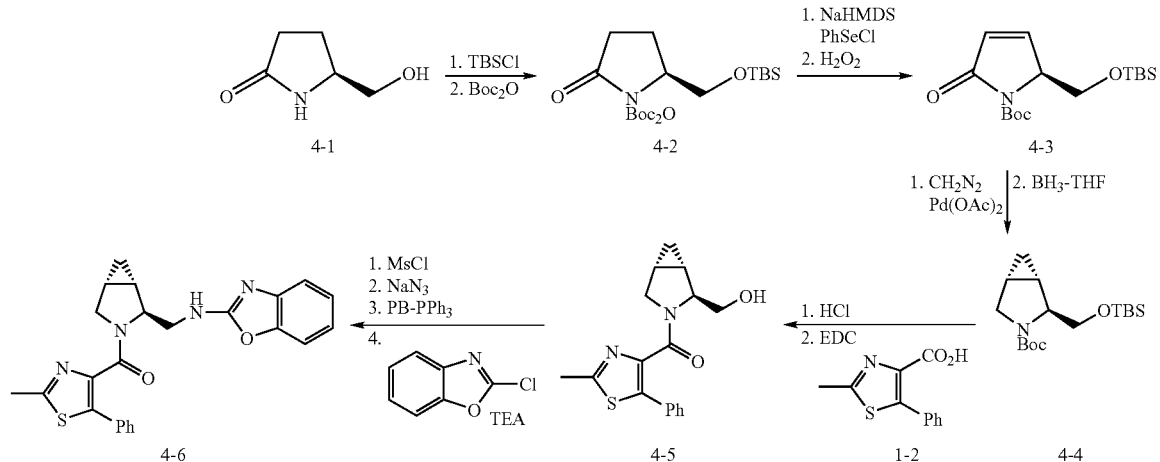

tert-butyl(2S)-2-({[tert-butyl(dimethyl)silyl]oxy}methyl)-5-oxopyrrolidine-1-carboxylate (4-2)

To a solution of (5S)-5-(hydroxymethyl)pyrrolidin-2-one (4-1, 7.4 g, 64.3 mmol) in CH$_2$Cl$_2$ (210 mL) at ambient temperature was added triethylamine (9.8 g, 96 mmol), 4-DMAP (0.79 g, 6.4 mmol), and tert-butyldimethylsilyl chloride (11.6 g, 77 mmol). The reaction was stirred 24 hours and quenched with saturated NH$_4$Cl (100 mL). The reaction was extracted with CH$_2$Cl$_2$ (2×200 mL), dried over magnesium sulfate and concentrated. The residue was purified by normal phase silica gel chromatography (0 to 100% EtOAc in hexanes) to afford the silylated product as an oil. The oil was with EtOAc (3×200 mL) and the combined organic phase was dried over magnesium sulfate and concentrated. The residue was purified by normal phase silica gel chromatography (0 to 70% EtOAc in hexanes) to afford the product (4-3) as an off-white solid. ESI+ MS: [M-Boc+H]$^+$ 228.3.

tert-butyl (1S,2S,5R)-2-({[tert-butyl(dimethyl)silyl]oxy}methyl)-3-azabicyclo[3.1.0]hexane-3-carboxylate (4-4)

To a solution of 4-3 (0.25 g, 0.76 mmol) in diethyl ether (3.8 mL) at 0° C. was added a solution of CH$_2$N$_2$ (7.6 mmol, made from treatment of 1-methyl-3-nitro-1-nitrosoguanidine with 40% KOH) in diethyl ether (5 mL) under nitrogen and the reaction mixture was stirred 2 h. The reaction was dried over magnesium sulfate and concentrated directly to yield an oil of >90% purity. The product was used without further purification. The oil was resuspended in THF (1.7 mL) at ambient temperature and to the mixture was added borane-tetrahydrofuran complex in THF (2.4 mL, 2.4 mmol, 1.0M solution). The reaction was stirred 15 h and quenched with methanol (2 mL). The combined organic phase was dried over magnesium sulfate and concentrated. The residue was purified by normal phase silica gel chromatography (0 to 65% EtOAc in hexanes) to afford the product (4-4) as an oil.

{(1S,2S,5R)-3-[(2-methyl-5-phenyl-1,3-thiazol-4-yl)carbonyl]-3-azabicyclo[3.1.0]hex-2-yl}methanol (4-5)

To a solution of 4-4 (0.175 g, 0.534 mmol) in dioxane (1.4 mL) at 25° C. was added a solution of HCl in dioxane (1.33 mL, 5.34 mmol, 4M in dioxane) and the reaction mixture was stirred 2 h. The reaction concentrated directly to afford a white solid. The white solid was resuspended in $CH_2Cl_2$ (1.4 mL) at ambient temperature and to the mixture was added 1-2 (0.141 g, 0.641 mmol), triethylamine (0.27 g, 2.7 mmol), EDC (0.154 g, 0.801 mmol) and HOBT (0.123 g, 0.801 mmol). The reaction was stirred 15 h and quenched with saturated $NaHCO_3$ (5 mL). The reaction mixture was diluted with EtOAc (20 mL) and washed with saturated $NaHCO_3$ (3×15 mL). The combined organic phase was dried over magnesium sulfate and concentrated. The residue was purified by normal phase silica gel chromatography (0 to 100% EtOAc in hexanes, then 0 to 25% MeOH in EtOAc) to afford the product (4-5) as a foamy solid. ESI+ MS: $[M+H]^+$ 315.2.

N-({(1S,2S,5R)-3-[(2-methyl-5-phenyl-1,3-thiazol-4-yl)carbonyl]-3-azabicyclo[3.1.0]hex-2-yl}methyl)-1,3-benzoxazol-2-amine (4-6)

To a solution of 4-5 (0.095 g, 0.30 mmol) in $CH_2Cl_2$ (1 mL) at ambient temperature was added triethylamine (0.15 g, 1.5 mmol) and methanesulfonyl chloride (0.052 g, 0.45 mmol) and the reaction was stirred for 0.5 hours. The reaction was quenched with water (5 mL) and the reaction was extracted with $CH_2Cl_2$ (10 mL). The organic phase was dried over magnesium sulfate and concentrated to afford an oil which was used without further purification. The residue was redissolved in DMF (1 mL) and to this solution was added sodium azide (0.20 g, 3.0 mmol) and the reaction was heated to 60° C. for 1 h. The reaction was cooled and diluted with EtOAc (15 mL). The organic phase was washed with water (3×10 mL), dried over magnesium sulfate and concentrated to an oil which was used without further purification. The residue was redissolved in THF (3 mL) at ambient temperature and to the solution was added polymer-bound triphenylphosphine (0.41 g, 0.91 mmol; 2.2 mmol/g loading) and water (0.11 g, 6.0 mmol). The reaction was stirred for 12 hours and quenched with magnesium sulfate. The reaction was filtered to yield a foamy solid of >90% purity. ESI+ MS: $[M+H]^+$ 314.3. The foamy solid was resuspended in DMF (1 mL) at ambient temperature was added triethylamine (0.058 g, 0.57 mmol) and 2-chlorobenzoxazole (0.041 g, 0.27 mmol) and the reaction was heated for 3 hours at 65° C. The reaction was cooled and quenched with water (10 mL) and diluted with EtOAc (20 mL). The organic phases were washed with water (3×10 mL) and dried over magnesium sulfate. The residue was purified by normal phase silica gel chromatography (0 to 100% EtOAc in hexanes, then 0 to 20% MeOH in EtOAc) to afford the product as a foamy, off-white solid. HRMS [M+H] $C_{24}H_{22}N_4O_2S_1$ calc'd 431.1536, found 431.1527.

EXAMPLE 5

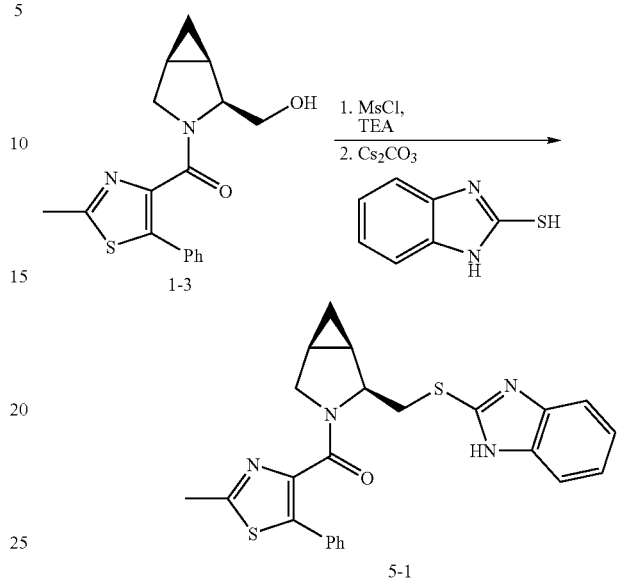

2-[({(1R,2S,5S)-3-[(2-methyl-5-phenyl-1,3-thiazol-4-yl)carbonyl]-3-azabicyclo[3.1.0]hex-2-yl}methyl)thio]-1H-benzimidazole (5-1)

To a solution of 1-3 (0.16 g, 0.51 mmol) in $CH_2Cl_2$ (2.5 mL) at ambient temperature was added triethylamine (0.10 g, 1.0 mmol) and methanesulfonyl chloride (0.087 g, 0.76 mmol) and the reaction was stirred for 0.5 hours. The reaction was quenched with water (5 mL) and the reaction was extracted with $CH_2Cl_2$ (10 mL). The organic phase was dried over magnesium sulfate and concentrated to afford an oil which was used without further purification. The residue was redissolved in DMF (2 mL) and to this solution was added 2-mercaptobenzimidazole (0.13 g, 0.86 mmol) and the reaction was heated to 60° C. for 18 h. The reaction was cooled and diluted with EtOAc (15 mL). The organic phase was washed with water (3×10 mL), dried over magnesium sulfate and concentrated. The residue was purified by normal phase silica gel chromatography (0 to 100% EtOAc in hexanes) to afford the product as a foamy, off-white solid. $^1$H NMR (500 MHz, $CDCl_3$) δ 7.65-7.40 (m, 7H), 7.24-7.17 (m, 2H), 4.53 (dd, J=10.0, 5.0 Hz, 1H), 4.19-4.14 (m, 11-1), 3.59 (dd, J=10.5, 5.0 Hz, 1H), 3.43 (d, J=10.5 Hz, 1H), 2.80 (s, 3H), 2.79-2.75 (m, 1H), 2.12-2.07 (m, 1H), 1.65-1.60 (m, 1H), 0.77-0.72 (m, 1H), 0.05-0.00 (m, 1H). HRMS [M+H] $C_{24}H_{22}N_4O_1S_2$ calc'd 447.1323, found 447.1308.

EXAMPLE 6

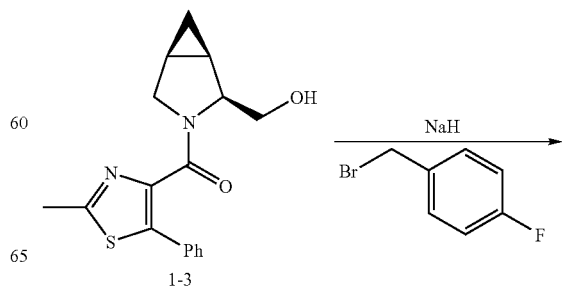

(1R,2S,5S)-2-{[(4-fluorobenzyl)oxy]methyl}-3-[(2-methyl-5-phenyl-1,3-thiazol-4-yl)carbonyl]-3-azabicyclo[3.1.0]hexane (6-1)

To a solution of {(1R,2S,5S)-3-[(2-methyl-5-phenyl-1,3-thiazol-4-yl)carbonyl]-3-azabicyclo[3.1.0]hex-2-yl}methanol (0.025 g, 0.080 mmol) in THF (0.50 mL) at 0° C. was added sodium hydride (60% dispersion in mineral oil, 0.008 g, 0.206 mmol) followed by 4-fluorobenzylbromide (0.039 g, 0.206 mmol) and the system was stirred at 0° C. for 3 h. The mixture was then quenched with ice, extracted with EtOAc, purified using reverse phase conditions (5%→85% 0.1% TFA in water: 0.1% TFA in acetonitrile) followed by free basing with saturated sodium carbonate to afford the title compound as a clear oil. $^1$H NMR (500 MHz, CDCl$_3$) δ 7.43-7.42 (m, 2H), 7.36-7.33 (m, 4H), 7.08-7.02 (m, 3H), 4.64 (m, 1H), 4.52 (m, 1H), 4.43 (m, 2H), 3.42 (m, 1H), 3.29 (m, 1H), 3.14 (m, 1H), 2.71 (s, 3H), 1.84 (m, 1H), 1.60 (m, 1H), 1.43 (m, 1H), 0.560 (m, 1H). HRMS [M+H] C$_{24}$H$_{23}$F$_1$N$_2$O$_2$S$_1$ calc'd 423.1537, found 423.1542.

EXAMPLE 7

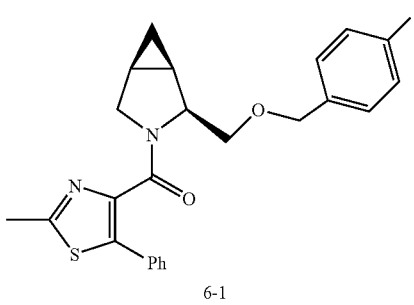

6-1

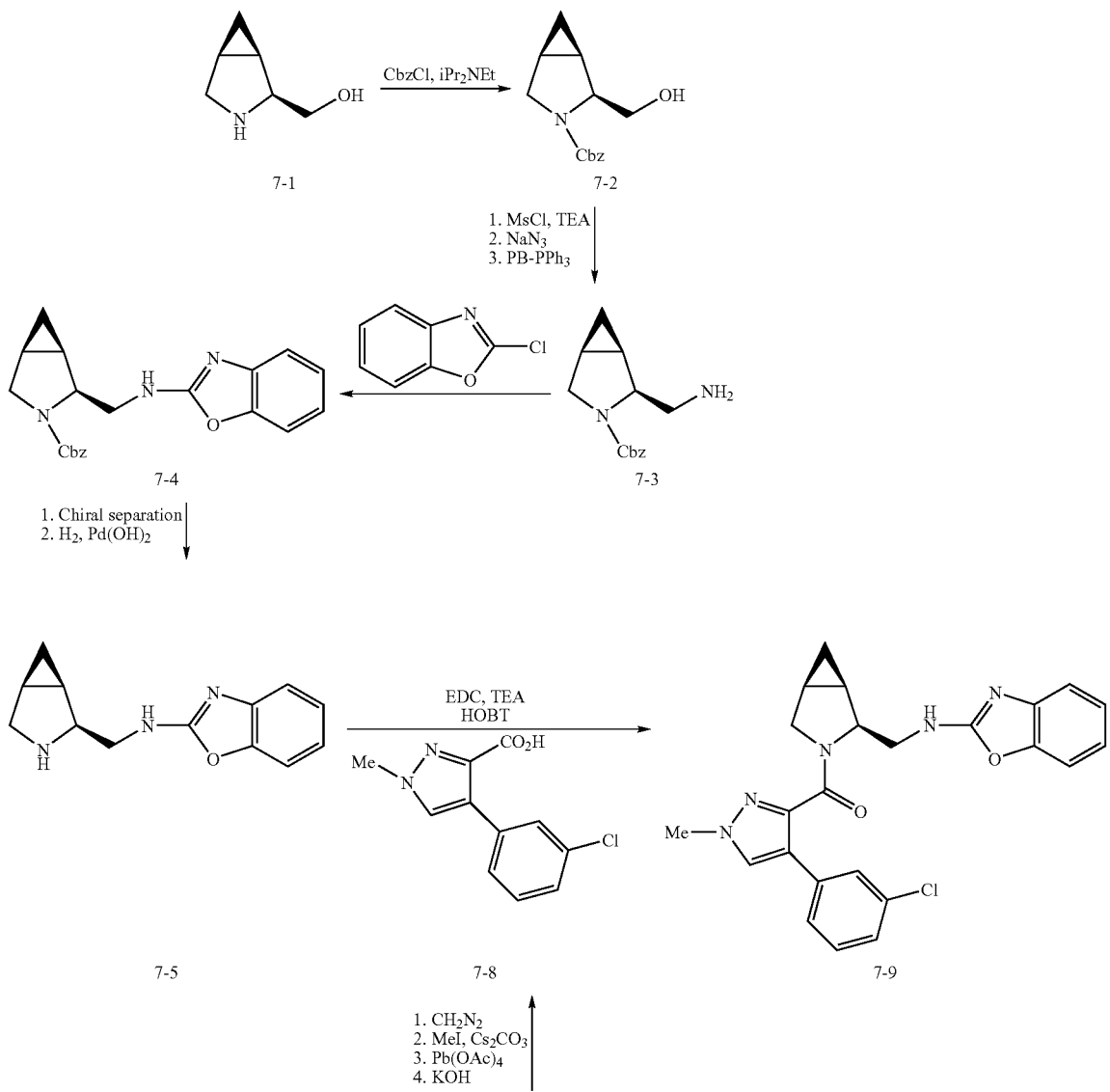

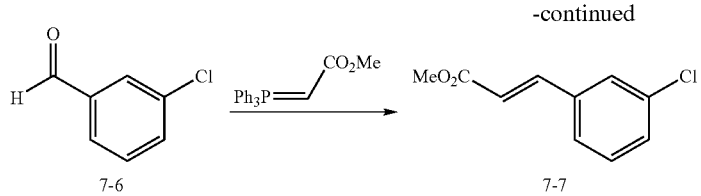

Racemic—benzyl (1R,2S,5S)-2-(hydroxymethyl)-3-azabicyclo[3.1.0]hexane-3-carboxylate (7-2)

To a solution of racemic 7-1 (7.2 g, 63.6 mmol, synthesized as in Example 1) in dichloromethane (320 mL) at 0° C. was added diisopropylethylamine (10.7 g, 83.0 mmol) followed by CbzCl (11.9 g, 70.0 mmol) and the reaction mixture was slowly warmed to ambient temperature over 48 h. The mixture was then quenched with water and extracted with dichloromethane. The combined organic layers were dried over $MgSO_4$ and concentrated to an oil. The oil was purified by normal phase silica gel chromatography (0 to 100% EtOAc in hexanes) to afford the product as an oil. ESI+ MS: $[M+H]^+$ 248.3.

Racemic—benzyl (1R,2S,5S)-2-(aminomethyl)-3-azabicyclo[3.1.0]hexane-3-carboxylate (7-3)

To a solution of racemic 7-2 (9.6 g, 38.8 mmol) in dichloromethane (190 mL) at 0° C. was added triethylamine (7.86 g, 78.0 mmol) followed by methanesulfonyl chloride (6.67 g, 58.2 mmol) and the reaction mixture was slowly warmed to ambient temperature over 24 h. The mixture was then quenched with water and extracted with dichloromethane. The combined organic layers were dried over $MgSO_4$ and concentrated to an oil. The residue was dissolved in dimethylformamide (100 mL) and to this mixture was added sodium azide (10.1 g, 155 mmol). The reaction mixture was heated to 90° C. for 15 h. The reaction was cooled and partition between EtOAc (300 mL) and water (100 mL). The organic phase was washed with water (3×100 mL), and the organic phase was dried over $MgSO_4$ and concentrated to an oil. The oil was dissolved in THF (370 mL) and to this was added polymer-bound triphenylphosphine (18.4 g, 40.4 mmol, 2.2 mmol/g loading) and water (6.6 g, 367 mmol). The reaction was heated to 50° C. for 2 h and the reaction was complete. The reaction was cooled to ambient temperature dried over $MgSO_4$ and concentrated to yield >80% pure product as an oil which was used as is in the next reaction. ESI+ MS: $[M+H]^+$ 247.4.

Racemic—benzyl (1R,2S,5S)-2-[(1,3-benzoxazol-2-ylamino)methyl]-3-azabicyclo[3.1.0]hexane-3-carboxylate (7-4)

To a solution of racemic 7-3 (6.3 g, 25.6 mmol) in dimethylformamide (100 mL) at 25° C. was added triethylamine (3.88 g, 38.4 mmol) followed by 2-chlorobenzoxazole (5.11 g, 33.3 mmol) and the reaction mixture was stirred at ambient temperature for 24 h. The mixture was diluted with EtOAc (400 mL) and washed with water (4×100 mL). The combined organic layers were dried over $MgSO_4$ and concentrated to an oil. The oil was purified by normal phase silica gel chromatography (0 to 100% EtOAc in hexanes) to afford the racemic product as an oil. ESI+ MS: $[M+H]^+$ 364.3. This material was then separated into its respective enantiomers by the following method: ChiralPak AD 2×25 cm, 10 uM (40:60 hexane: EtOH, 0.1% diethylamine; flow rate=8 mL/min). Enantiomer A Rt=7.3 min; Enantiomer B Rt=8.7 min. $^1$H NMR (500 MHz, $CDCl_3$) δ 7.43-7.42 (m, 2H), 7.36-7.33 (m, 4H), 7.08-7.02 (m, 3H), 4.64 (m, 1H), 4.52 (m, 1H), 4.43 (m, 2H), 3.42 (m, 1H), 3.29 (m, 1H), 3.14 (m, 1H), 2.71 (s, 3H), 1.84 (m, 1H), 1.60 (m, 1H), 1.43 (m, 1H), 0.560 (m, 1H). HRMS [M+H] $C_{24}H_{23}F_1N_2O_2S_1$ calc'd 423.1537, found 423.1542.

Enantiomer A—[(1R,2S,5S)-3-azabicyclo[3.1.0]hexy-2-ylmethyl]-1,3-benzoxazol-2-amine (7-5)

To a solution of enantiomer A 7-4 (0.3 g, 0.83 mmol) in 1:1 EtOH/EtOAc (4.0 mL) at 25° C. was added $Pd(OH)_2$ (0.09 g, 0.14 mmol) and the reaction mixture was stirred at ambient temperature for 1 h. The mixture was filtered through a pad of celite and then concentrated in vacuo to afford the title compound as a cream solid. ESI+ MS: $[M+H]^+$ 230.0.

Methyl (2E)-3-(3-chlorophenyl)acrylate (7-7)

To a solution of 2-chlorobenzaldehyde 7-6 (5.0 g, 35.6 mmol) in toluene (50 mL) at 25° C. was added methyl(triphenylphosphoranylidene)acetate (13.0 g, 39.1 mmol) and the reaction mixture was stirred at 110° C. for 3 h. The mixture was concentrated in vacuo and purified by normal phase silica gel chromatography (0 to 20% EtOAc in hexanes) to afford the title compound a clear oil. ESI+ MS: $[M+H]^+$ 197.2.

4-(3-chlorophenyl)-1-methyl-1H-pyrazole-3-carboxylic acid (7-8)

To a vigorously stirred solution diethyl ether (215 mL) in 40% KOH (160 mL) in a plastic bottle at 0° C. was added 1-methyl-3-nitrosoguanidine (15.5 g, 105 mmol) over a period of 5 minutes and stirred for 0.5 h at 0° C. The mixture was then transferred to a plastic separatory funnel from which the aqueous phase was separated from the organic phase. The organic phase was then added very slowly over a period of 0.5 h to a plastic bottle containing a solution of 7-7 (6.4 g, 32.5 mmol) in diethyl ether (130 mL) at 0° C. and stirred overnight. The system was then bubbled through with nitrogen for 0.5 h and the reaction contents were poured in to a round bottom flask and the contents were concentrated in vacuo to yield a yellow solid. To a solution of this yellow solid (1.0 g, 4.19 mmol) in DMF (8 mL) at 25° C. was added cesium carbonate (2.04 g, 6.28 mmol) and iodomethane (0.314 mL, 5.0 mmol) and the system was stirred overnight. The mixture was diluted with EtOAc and washed with water. The combined organic layers were dried over $MgSO_4$ and concentrated to a gold oil. To this gold oil (1.0 g, 3.96 mmol) in DCM (8 mL) at 25° C. was added lead tetraacetate (2.63 g, 5.94 mmol) and the system was stirred for 2 h. The system was cooled to 0° C. and any excess lead tetraacetate was destroyed with a drop of acetic acid and 3 drops of hydrazine hydrate. The mixture was then dried over potassium carbonate, concentrated and purified by normal phase silica gel chromatography (0 to 100% EtOAc in hexanes) to afford a white solid.

To a solution of this white solid (0.466 g, 1.85 mmol) in THF (2.0 mL) and MeOH (2.0 mL) at 25° C. was added a 1M solution of KOH (2.79 mL, 2.79 mmol) and the system was stirred overnight. The mixture was then neutralized with 1N HCl to a pH of 5. Solvent was then removed in vacuo and the residue was azeotroped 2× with toluene to afford the title compound as a yellow powder. ESI+ MS: [M+H]$^+$ 237.2.

[(((1R,2S,5S)-3-{[4-(3-chlorophenyl)-1-methyl-1H-pyrazol-3-yl]carbonyl}-3-azabicyclo[3.1.0]hexy-2-yl)methyl]-1,3-benzoxazol-2-amine (7-9)

To a solution of 7-5 (0.05 g, 0.22 mmol) and 7-8 (0.05 g, 0.22 mmol) in dichloromethane (2 mL) at 25° C. was added EDC (0.05 g, 0.28 mmol), HOBt (0.04 g, 0.28 mmol) and triethylamine (0.1 mL, 0.76 mmol) and the reaction mixture was stirred at ambient temperature overnight. The mixture was diluted with EtOAc and washed with water. The combined organic layers were dried over MgSO$_4$, concentrated, and purified by normal phase silica gel chromatography (0 to 6% MeOH in EtOAc) to afford the title compound as a yellow foam. $^1$H NMR (500 MHz, CDCl$_3$) δ 7.54 (s, 1H), 7.37-7.40 (m, 2H), 7.24-7.31 (m, 4H), 7.15-7.18 (m, 1H), 7.01-7.05 (m, 1H), 4.43 (br s, 1H), 4.12-4.17 (m, 1H), 3.98 (s, 3H), 3.57-3.59 (m, 2H), 3.48-3.50 (m, 1H), 1.90-1.95 (m, 1H), 1.46-1.48 (m, 1H), 0.64-0.68 (m, 1H), 0.33-0.34 (m, 1H). HRMS [M+H] C$_{24}$H$_{22}$Cl$_1$N$_5$O$_2$ calc'd 448.1535, found 448.1533.

The following compounds were prepared using the foregoing methodology, but substituting the appropriately substituted reagent, such as organometallic or amine, as described in the foregoing Reaction Schemes and Examples. The requisite starting materials were commercially available, described in the literature or readily synthesized by one skilled in the art of organic synthesis without undue experimentation.

| Structure | Chemical Name | Found Mass (M + 1) |
|---|---|---|
| 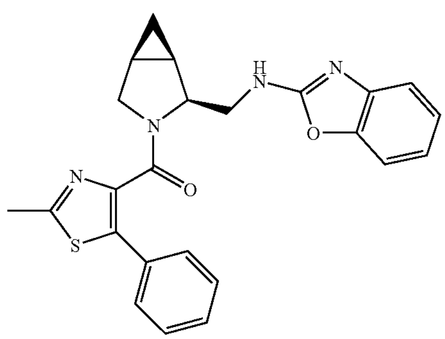 | N-({(1R,2S,5S)-3-[(2-methyl-5-phenyl-1,3-thiazol-4-yl)carbonyl]-3-azabicyclo[3.1.0]hex-2-yl}methyl)-1,3-benzoxazol-2-amine | 431.1543 |
| 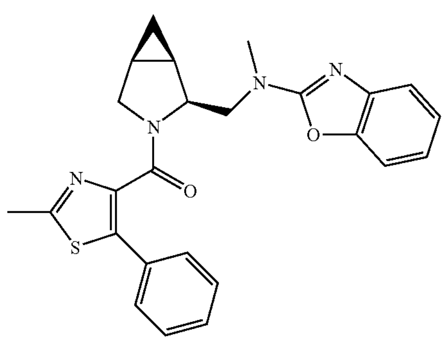 | N-methyl-N-({(1R,2S,5S)-3-[(2-methyl-5-phenyl-1,3-thiazol-4-yl)carbonyl]-3-azabicyclo[3.1.0]hex-2-yl}methyl)-1,3-benzoxazol-2-amine | 445.1698 |
| 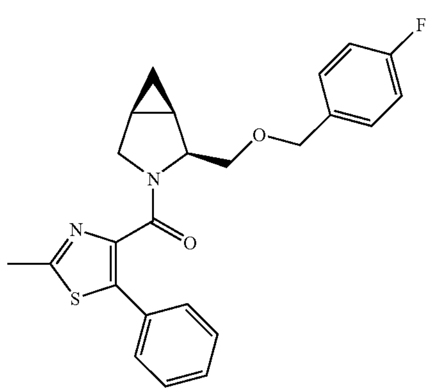 | (1R,2S,5S)-2-{[(4-fluorobenzyl)oxy]methyl}-3-[(2-methyl-5-phenyl-1,3-thiazol-4-yl)carbonyl]-3-azabicyclo[3.1.0]hexane | 423.1542 |

| Structure | Chemical Name | Found Mass (M + 1) |
|---|---|---|
| 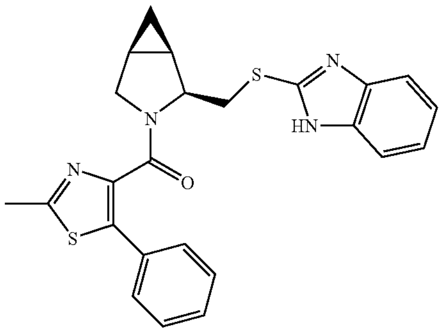 | 2-[({(1R,2S,5S)-3-[(2-methyl-5-phenyl-1,3-thiazol-4-yl)carbonyl]-3-azabicyclo[3.1.0]hex-2-yl}methyl)thio]-1H-benzimidazole | 447.1308 |
| 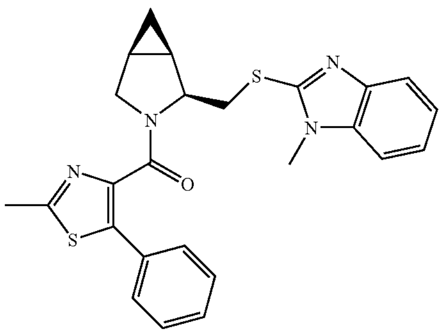 | 1-methyl-2-[({(1R,2S,5S)-3-[(2-methyl-5-phenyl-1,3-thiazol-4-yl)carbonyl]-3-azabicyclo[3.1.0]hex-2-yl}methyl)thio]-1H-benzimidazole | 461.1466 |
| 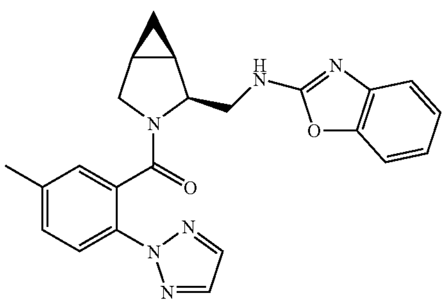 | N-({(1R,2S,5S)-3-[5-methyl-2-(2H-1,2,3-triazol-2-yl)benzoyl]-3-azabicyclo[3.1.0]hex-2-yl}methyl)-1,3-benzoxazol-2-amine | 415.1887 |
| 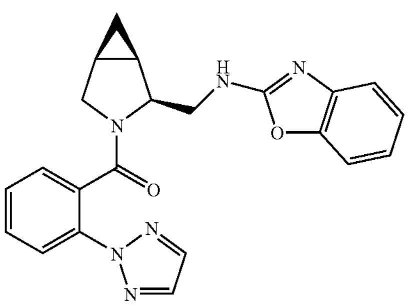 | N-({(1R,2S,5S)-3-[2-(2H-1,2,3-triazol-2-yl)benzoyl]-3-azabicyclo[3.1.0]hex-2-yl}methyl)-1,3-benzoxazol-2-amine | 423.1557 [M + Na] |
| 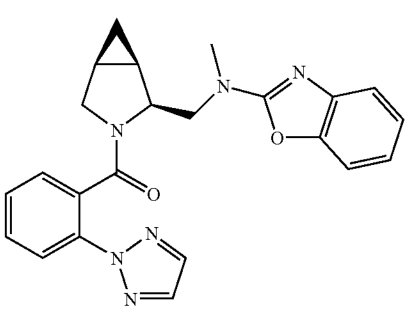 | N-methyl-N-({(1R,2S,5S)-3-[2-(2H-1,2,3-triazol-2-yl)benzoyl]-3-azabicyclo[3.1.0]hex-2-yl}methyl)-1,3-benzoxazol-2-amine | 415.1888 |

| Structure | Chemical Name | Found Mass (M + 1) |
|---|---|---|
| 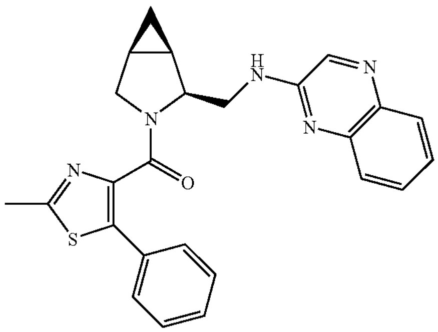 | N-({(1R,2S,5S)-3-[(2-methyl-5-phenyl-1,3-thiazol-4-yl)carbonyl]-3-azabicyclo[3.1.0]hex-2-yl}methyl)quinoxalin-2-amine | 442.1705 |
| 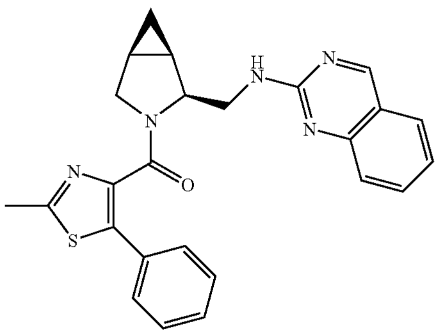 | N-({(1R,2S,5S)-3-[(2-methyl-5-phenyl-1,3-thiazol-4-yl)carbonyl]-3-azabicyclo[3.1.0]hex-2-yl}methyl)quinazolin-2-amine | 442.1703 |
| 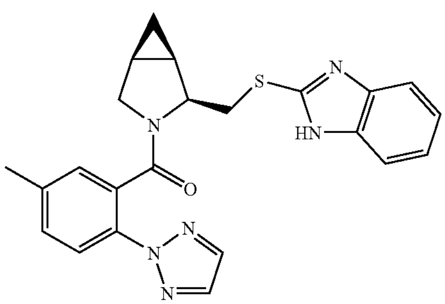 | 2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 431.1649 |
| 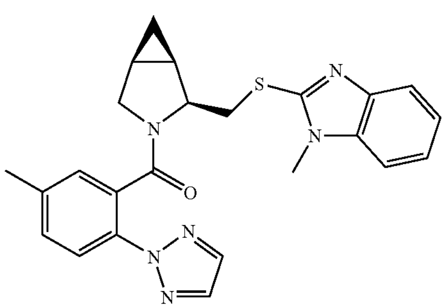 | 1-methyl-2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 445.1820 |

-continued

| Structure | Chemical Name | Found Mass (M + 1) |
|---|---|---|
| 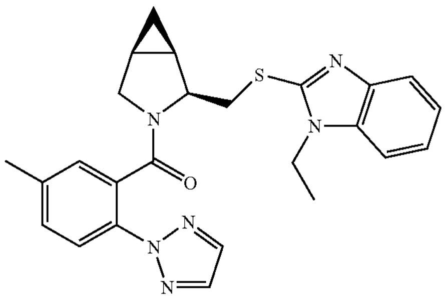 | 1-ethyl-2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 459.1959 |
| 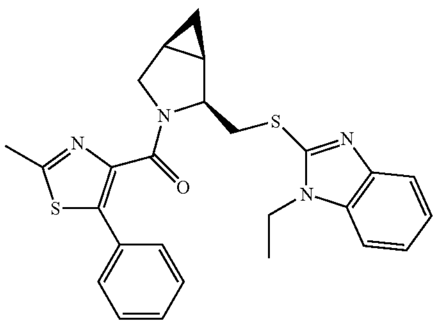 | 1-ethyl-2-[({(1R,2S,5S)-3-[(2-methyl-5-phenyl-1,3-thiazol-4-yl)carbonyl]-3-azabicyclo[3.1.0]hex-2-yl}methyl)thio]-1H-benzimidazole | 475.1626 |
| 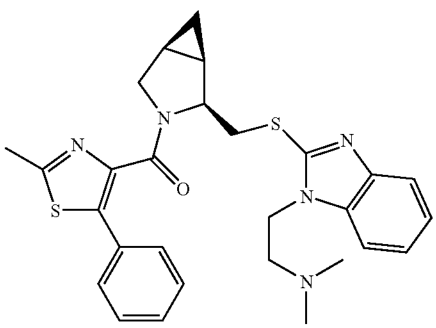 | N,N-dimethyl-2-{2-[({(1R,2S,5S)-3-[(2-methyl-5-phenyl-1,3-thiazol-4-yl)carbonyl]-3-azabicyclo[3.1.0]hex-2-yl}methyl)thio]-1H-benzimidazol-1-yl}ethanamine | 518.2051 |
| 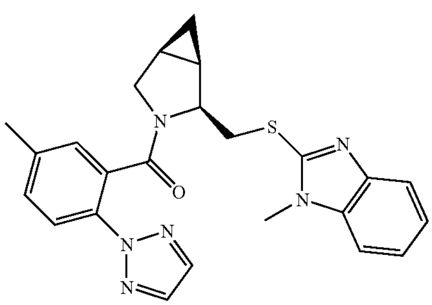 | 1-methyl-N-({(1R,2S,5S)-3-[5-methyl-2-(2H-1,2,3-triazol-2-yl)benzoyl]-3-azabicyclo[3.1.0]hex-2-yl}methyl)-1H-benzimidazol-2-amine | 428.2196 |
| 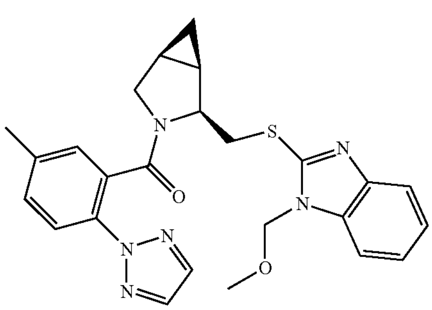 | 1-(methoxymethyl)-2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 475.1918 |

-continued

| Structure | Chemical Name | Found Mass (M + 1) |
|---|---|---|
| 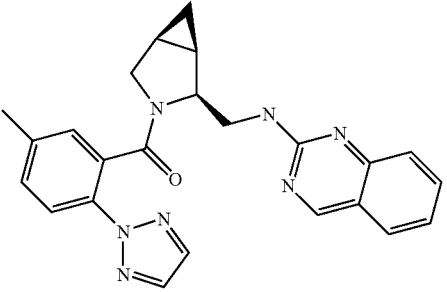 | N-({(1R,2S,5S)-3-[5-methyl-2-(2H-1,2,3-triazol-2-yl)benzoyl]-3-azabicyclo[3.1.0]hex-2-yl}methyl)quinazolin-2-amine | 426.2039 |
| 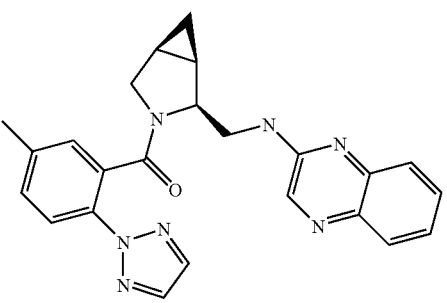 | N-({(1R,2S,5S)-3-[5-methyl-2-(2H-1,2,3-triazol-2-yl)benzoyl]-3-azabicyclo[3.1.0]hex-2-yl}methyl)quinoxalin-2-amine | 426.2039 |
| 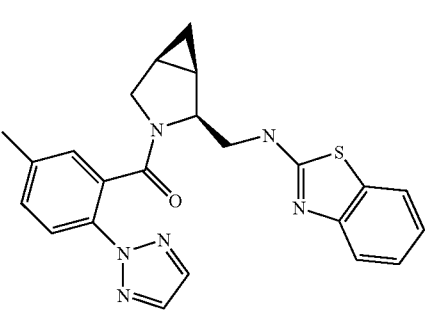 | N-({(1R,2S,5S)-3-[5-methyl-2-(2H-1,2,3-triazol-2-yl)benzoyl]-3-azabicyclo[3.1.0]hex-2-yl}methyl)-1,3-benzothiazol-2-amine | 431.1648 |
| 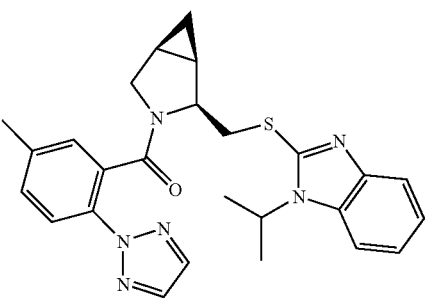 | 1-isopropyl-2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 473.2123 |
| 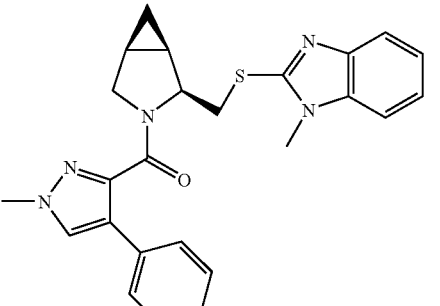 | 1-methyl-2-[({(1R,2S,5S)-3-[(1-methyl-4-phenyl-1H-pyrazol-3-yl)carbonyl]-3-azabicyclo[3.1.0]hex-2-yl}methyl)thio]-1H-benzimidazole | 444.1859 |

-continued

| Structure | Chemical Name | Found Mass (M + 1) |
|---|---|---|
| 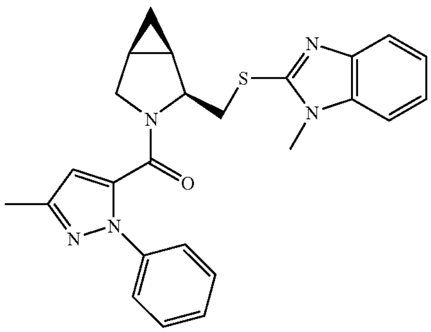 | 1-methyl-2-[({(1R,2S,5S)-3-[(3-methyl-1-phenyl-1H-pyrazol-5-yl)carbonyl]-3-azabicyclo[3.1.0]hex-2-yl}methyl)thio]-1H-benzimidazole | 444.1852 |
| 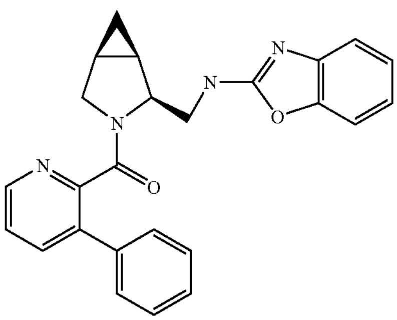 | N-({(1R,2S,5S)-3-[(3-phenylpyridin-2-yl)carbonyl]-3-azabicyclo[3.1.0]hex-2-yl}methyl)-1,3-benzoxazol-2-amine | 411.1796 |
| 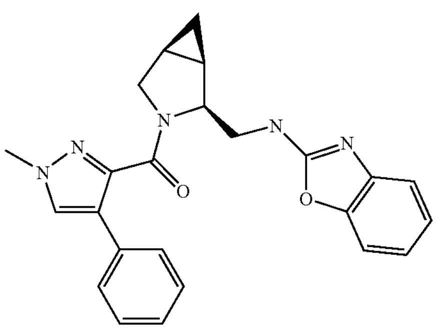 | N-({(1R,2S,5S)-3-[(1-methyl-4-phenyl-1H-pyrazol-3-yl)carbonyl]-3-azabicyclo[3.1.0]hex-2-yl}methyl)-1,3-benzoxazol-2-amine | 414.1910 |
| 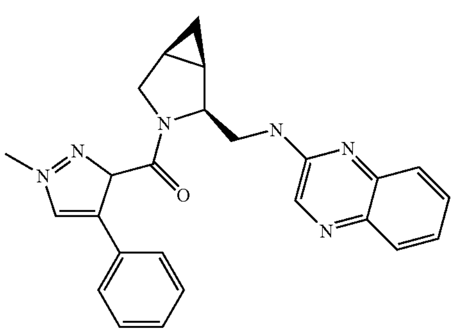 | N-({(1R,2S,5S)-3-[(1-methyl-4-phenyl-1H-pyrazol-3-yl)carbonyl]-3-azabicyclo[3.1.0]hex-2-yl}methyl)quinoxalin-2-amine | 425.2068 |

-continued

| Structure | Chemical Name | Found Mass (M + 1) |
|---|---|---|
| 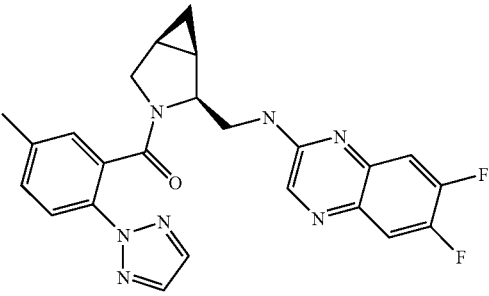 | 6,7-difluoro-N-({(1R,2S,5S)-3-[5-methyl-2-(2H-1,2,3-triazol-2-yl)benzoyl]-3-azabicyclo[3.1.0]hex-2-yl}methyl)quinoxalin-2-amine | 462.1857 |
| 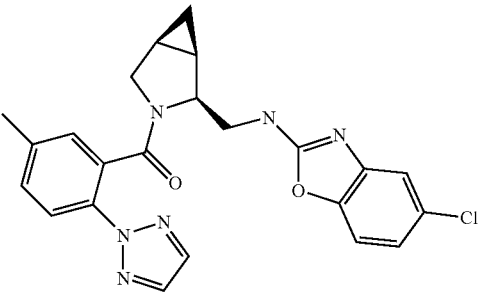 | 5-chloro-N-({(1R,2S,5S)-3-[5-methyl-2-(2H-1,2,3-triazol-2-yl)benzoyl]-3-azabicyclo[3.1.0]hex-2-yl}methyl)-1,3-benzoxazol-2-amine | 449.1481 |
| 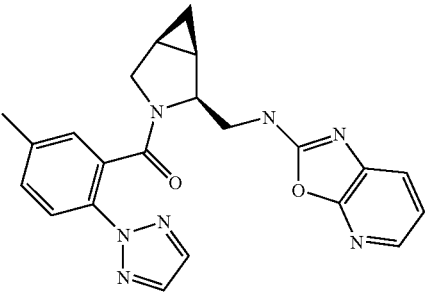 | N-({(1R,2S,5S)-3-[5-methyl-2-(2H-1,2,3-triazol-2-yl)benzoyl]-3-azabicyclo[3.1.0]hex-2-yl}methyl)[1,3]oxazolo[5,4-b]pyridin-2-amine | 416.1816 |
| 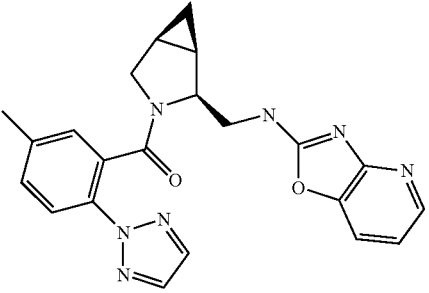 | N-({(1R,2S,5S)-3-[5-methyl-2-(2H-1,2,3-triazol-2-yl)benzoyl]-3-azabicyclo[3.1.0]hex-2-yl}methyl)[1,3]oxazolo[4,5-b]pyridin-2-amine | 416.1815 |
| 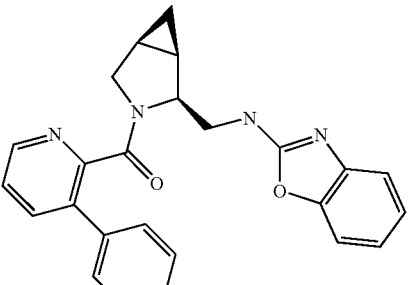 | N-{[(1R,2S,5S)-3-(3,3'-bipyridin-2-ylcarbonyl)-3-azabicyclo[3.1.0]hex-2-yl]methyl}-1,3-benzoxazol-2-amine | 412.1754 |

-continued

| Structure | Chemical Name | Found Mass (M + 1) |
|---|---|---|
| 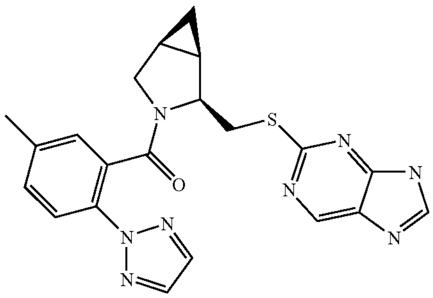 | 2-[({(1R,2S,5S)-3-[5-methyl-2-(2H-1,2,3-triazol-2-yl)benzoyl]-3-azabicyclo[3.1.0]hex-2-yl}methyl)thio]-9H-purine | 433.1552 |
| 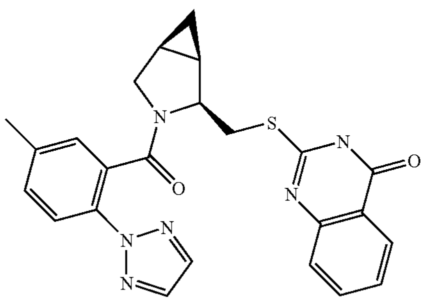 | 2-[({(1R,2S,5S)-3-[5-methyl-2-(2H-1,2,3-triazol-2-yl)benzoyl]-3-azabicyclo[3.1.0]hex-2-yl}methyl)thio]quinazolin-4(3H)-one | 459.1595 |
| 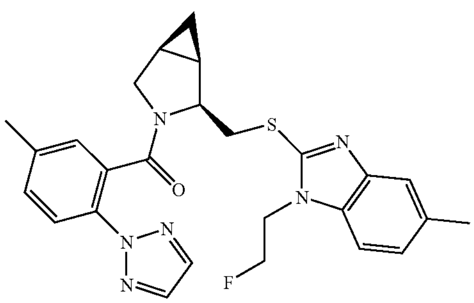 | 1-(2-fluoroethyl)-5-methyl-2-[({(1R,2S,5S)-3-[5-methyl-2-(2H-1,2,3-triazol-2-yl)benzoyl]-3-azabicyclo[3.1.0]hex-2-yl}methyl)thio]-1H-benzimidazole | 491.2007 |
| 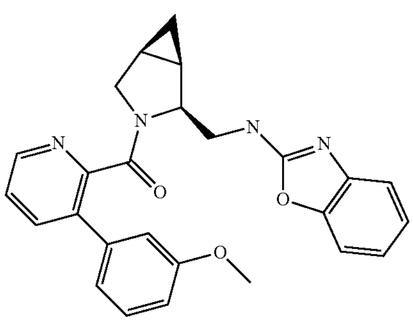 | N-[((1R,2S,5S)-3-{[3-(3-methoxyphenyl)pyridin-2-yl]carbonyl}-3-azabicyclo[3.1.0]hex-2-yl)methyl]-1,3-benzoxazol-2-amine | 441.1909 |
| 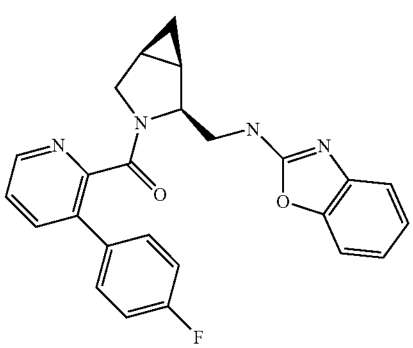 | N-[((1R,2S,5S)-3-{[3-(4-fluorophenyl)pyridin-2-yl]carbonyl}-3-azabicyclo[3.1.0]hex-2-yl)methyl]-1,3-benzoxazol-2-amine | 429.1712 |

| Structure | Chemical Name | Found Mass (M + 1) |
|---|---|---|
| 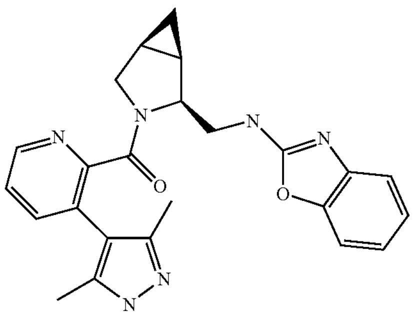 | N-[((1R,2S,5S)-3-{[3-(3,5-dimethyl-1H-pyrazol-4-yl)pyridin-2-yl]carbonyl}-3-azabicyclo[3.1.0]hex-2-yl)methyl]-1,3-benzoxazol-2-amine | 429.2023 |
| 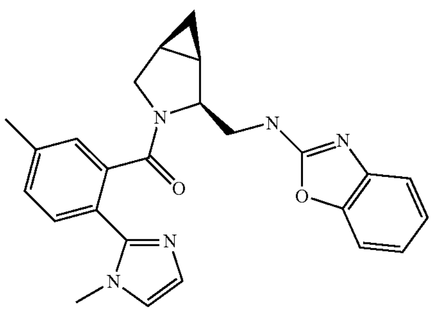 | N-({(1R,2S,5S)-3-[5-methyl-2-(1-methyl-1H-imidazol-2-yl)benzoyl]-3-azabicyclo[3.1.0]hex-2-yl}methyl)-1,3-benzoxazol-2-amine | 428.2078 |
| 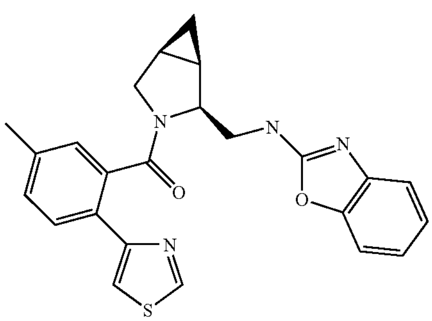 | N-({(1R,2S,5S)-3-[5-methyl-2-(1,3-thiazol-4-yl)benzoyl]-3-azabicyclo[3.1.0]hex-2-yl}methyl)-1,3-benzoxazol-2-amine | 431.1522 |
| 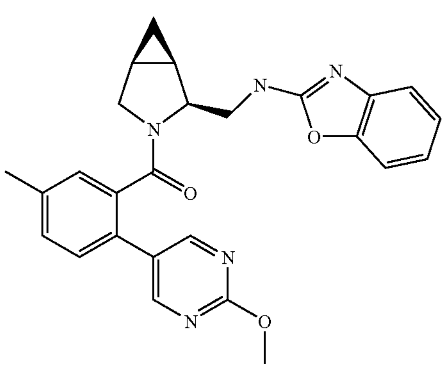 | N-({(1R,2S,5S)-3-[2-(2-methoxypyrimidin-5-yl)-5-methylbenzoyl]-3-azabicyclo[3.1.0]hex-2-yl}methyl)-1,3-benzoxazol-2-amine | 456.2003 |

-continued

| Structure | Chemical Name | Found Mass (M + 1) |
|---|---|---|
| 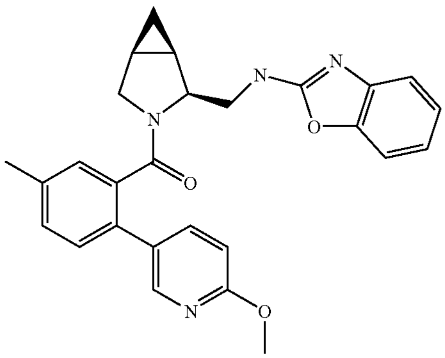 | N-({(1R,2S,5S)-3-[2-(6-methoxypyridin-3-yl)-5-methylbenzoyl]-3-azabicyclo[3.1.0]hex-2-yl}methyl)-1,3-benzoxazol-2-amine | 455.2078 |
| 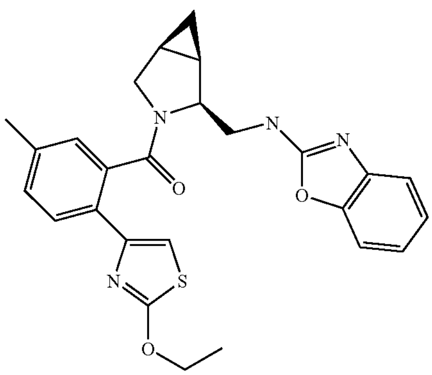 | N-({(1R,2S,5S)-3-[2-(2-ethoxy-1,3-thiazol-4-yl)-5-methylbenzoyl]-3-azabicyclo[3.1.0]hex-2-yl}methyl)-1,3-benzoxazol-2-amine | 475.1782 |
| 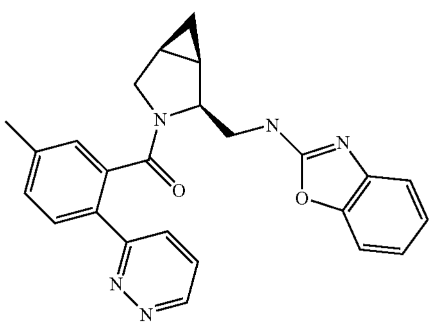 | N-{[(1R,2S,5S)-3-(5-methyl-2-pyridazin-3-ylbenzoyl)-3-azabicyclo[3.1.0]hex-2-yl]methyl}-1,3-benzoxazol-2-amine | 426.1910 |
| 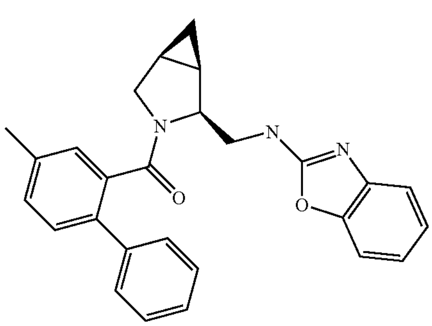 | N-({(1R,2S,5S)-3-[(4-methylbiphenyl-2-yl)carbonyl]-3-azabicyclo[3.1.0]hex-2-yl}methyl)-1,3-benzoxazol-2-amine | 424.1995 |

-continued

| Structure | Chemical Name | Found Mass (M + 1) |
|---|---|---|
| 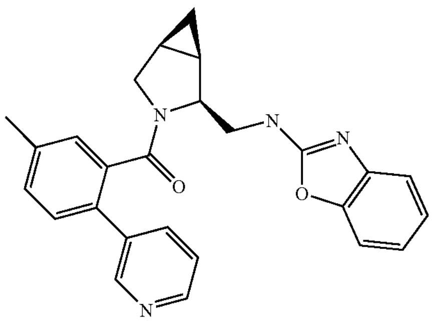 | N-{[(1R,2S,5S)-3-(5-methyl-2-pyridin-3-ylbenzoyl)-3-azabicyclo[3.1.0]hex-2-yl]methyl}-1,3-benzoxazol-2-amine | 425.1959 |
| 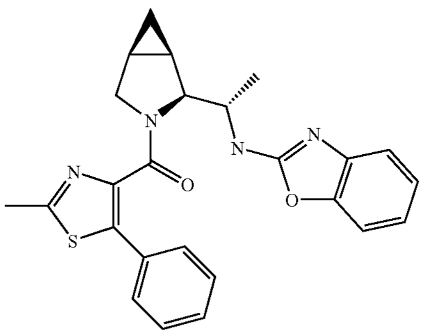 | N-((1 S)-1-{(1R,2S,5S)-3-[(2-methyl-5-phenyl-1,3-thiazol-4-yl)carbonyl]-3-azabicyclo[3.1.0]hex-2-yl}ethyl)-1,3-benzoxazol-2-amine | 445.1674 |
| 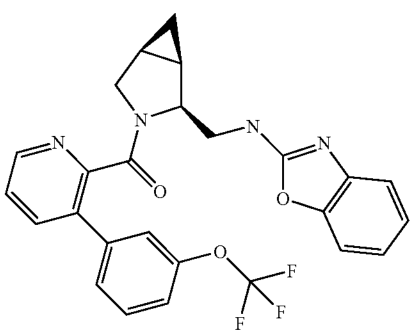 | N-{[(1R,2S,5S)-3-({3-[3-(trifluoromethoxy)phenyl]pyridin-2-yl}carbonyl)-3-azabicyclo[3.1.0]hex-2-yl]methyl}-1,3-benzoxazol-2-amine | 495.1627 |
| 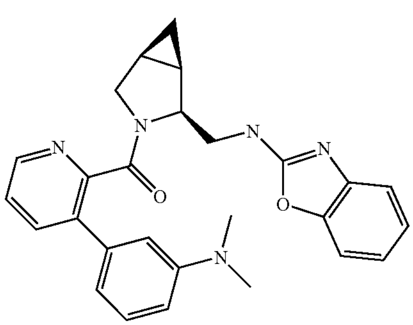 | N-{[(1R,2S,5S)-3-({3-[3-(dimethylamino)phenyl]pyridin-2-yl}carbonyl-3-azabicyclo[3.1.0]hex-2-yl]methyl}-1,3-benzoxazol-2-amine | 454.2231 |

| Structure | Chemical Name | Found Mass (M + 1) |
|---|---|---|
| 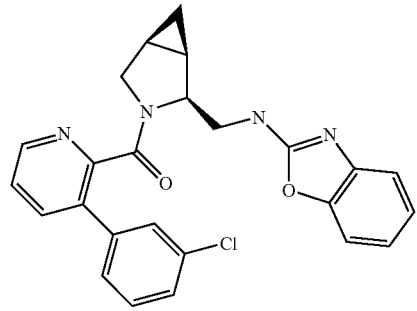 | N-[((1R,2S,5S)-3-{[3-(3-chlorophenyl)pyridin-2-yl]carbonyl}-3-azabicyclo[3.1.0]hex-2-yl)methyl]-1,3-benzoxazol-2-amine | 445.1422 |
| 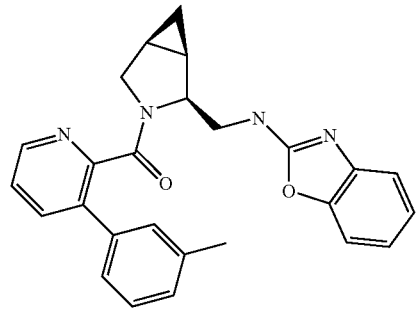 | N-[((1R,2S,5S)-3-{[3-(3-methylphenyl)pyridin-2-yl]carbonyl}-3-azabicyclo[3.1.0]hex-2-yl)methyl]-1,3-benzoxazol-2-amine | 425.1960 |
| 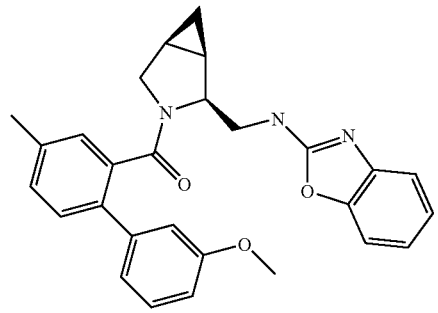 | N-({(1R,2S,5S)-3-[(3'-methoxy-4-methylbiphenyl-2-yl)carbonyl]-3-azabicyclo[3.1.0]hex-2-yl}methyl)-1,3-benzoxazol-2-amine | 454.2113 |
| 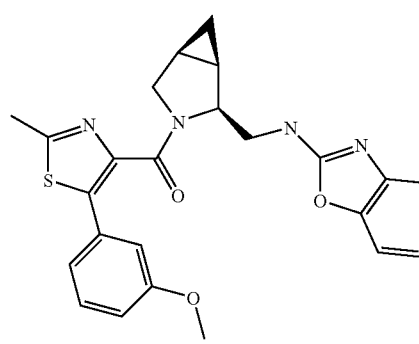 | N-[((1R,2S,5S)-3-{[5-(3-methoxyphenyl)-2-methyl-1,3-thiazol-4-yl]carbonyl}-3-azabicyclo[3.1.0]hex-2-yl)methyl]-1,3-benzoxazol-2-amine | 461.1627 |

-continued

| Structure | Chemical Name | Found Mass (M + 1) |
|---|---|---|
| 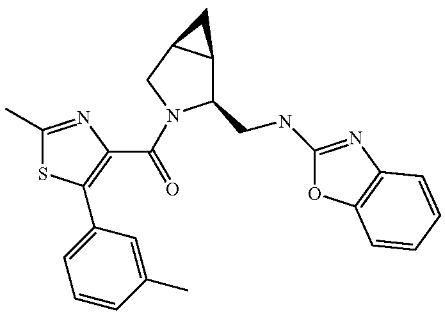 | N-[((1R,2S,5S)-3-{[2-methyl-5-(3-methylphenyl)-1,3-thiazol-4-yl]carbonyl}-3-azabicyclo[3.1.0]hex-2-yl)methyl]-1,3-benzoxazol-2-amine | 445.1675 |
| 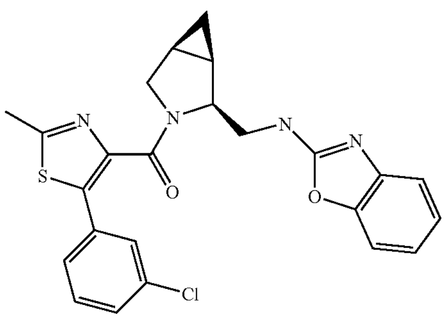 | N-[((1R,2S,5S)-3-{[5-(3-chlorophenyl)-2-methyl-1,3-thiazol-4-yl]carbonyl}-3-azabicyclo[3.1.0]hex-2-yl)methyl]-1,3-benzoxazol-2-amine | 465.1128 |
| 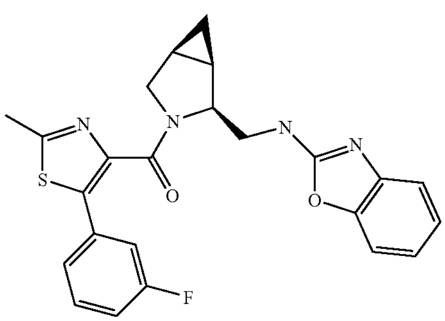 | N-[((1R,2S,5S)-3-{[5-(3-fluorophenyl)-2-methyl-1,3-thiazol-4-yl]carbonyl}-3-azabicyclo[3.1.0]hex-2-yl)methyl]-1,3-benzoxazol-2-amine | 449.1427 |
| 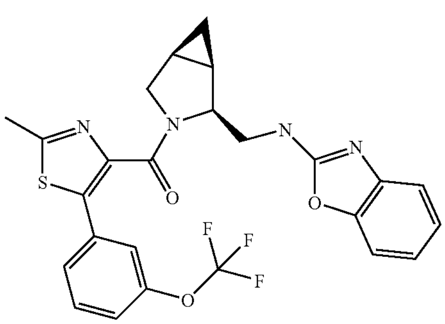 | N-{[(1R,2S,5S)-3-({2-methyl-5-[3-(trifluoromethoxy)phenyl]-1,3-thiazol-4-yl}carbonyl)-3-azabicyclo[3.1.0]hex-2-yl]methyl}-1,3-benzoxazol-2-amine | 515.1333 |

-continued

| Structure | Chemical Name | Found Mass (M + 1) |
|---|---|---|
| 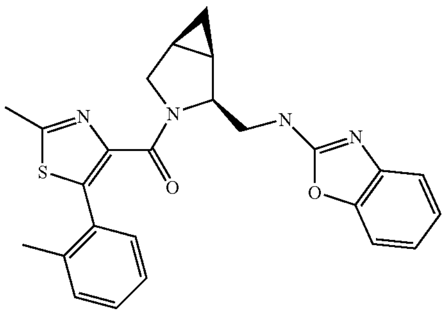 | N-[((1R,2S,5S)-3-{[2-methyl-5-(2-methylphenyl)-1,3-thiazol-4-yl]carbonyl}-3-azabicyclo[3.1.0]hex-2-yl)methyl]-1,3-benzoxazol-2-amine | 445.1679 |
| 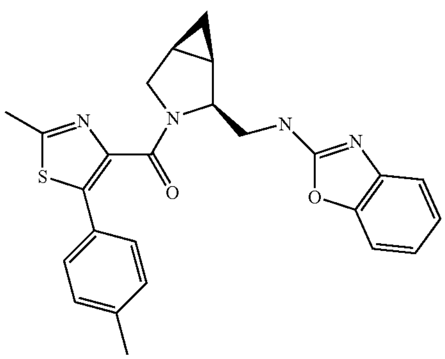 | N-[((1R,2S,5S)-3-{[2-methyl-5-(4-methylphenyl)-1,3-thiazol-4-yl]carbonyl}-3-azabicyclo[3.1.0]hex-2-yl)methyl]-1,3-benzoxazol-2-amine | 445.1679 |
| 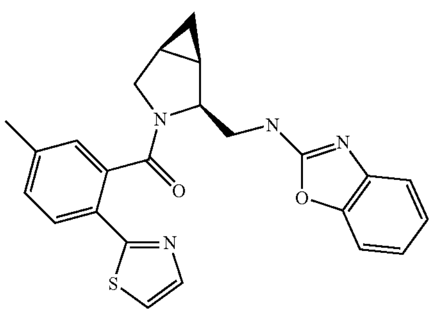 | N-({(1R,2S,5S)-3-[5-methyl-2-(1,3-thiazol-2-yl)benzoyl]-3-azabicyclo[3.1.0]hex-2-yl}methyl)-1,3-benzoxazol-2-amine | 431.1526 |
| 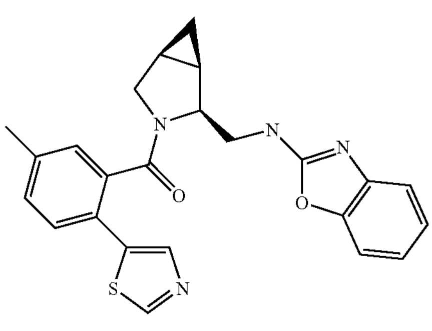 | N-({(1R,2S,5S)-3-[5-methyl-2-(1,3-thiazol-5-yl)benzoyl]-3-azabicyclo[3.1.0]hex-2-yl}methyl)-1,3-benzoxazol-2-amine | 431.1527 |

| Structure | Chemical Name | Found Mass (M + 1) |
|---|---|---|
| 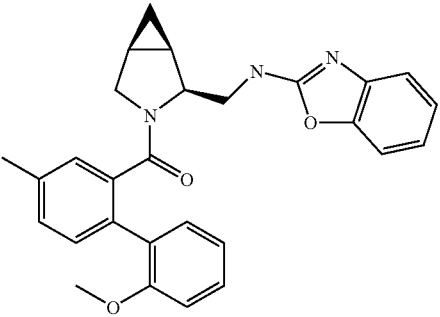 | N-({(1R,2S,5S)-3-[(2'-methoxy-4-methylbiphenyl-2-yl)carbonyl]-3-azabicyclo[3.1.0]hex-2-yl}methyl)-1,3-benzoxazol-2-amine | 454.2116 |
| 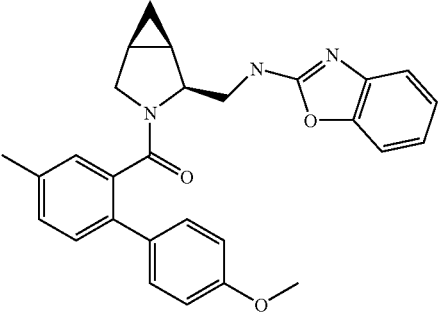 | N-({(1R,2S,5S)-3-[(4'-methoxy-4-methylbiphenyl-2-yl)carbonyl]-3-azabicyclo[3.1.0]hex-2-yl}methyl)-1,3-benzoxazol-2-amine | 454.2115 |
| 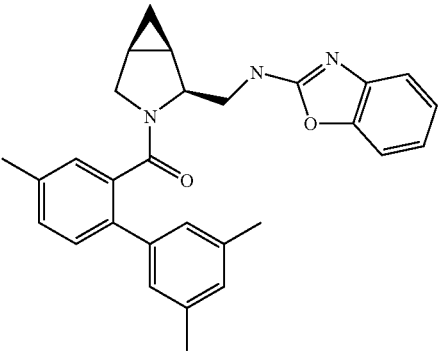 | N-({(1R,2S,5S)-3-[(3',4,5'-trimethylbiphenyl-2-yl)carbonyl]-3-azabicyclo[3.1.0]hex-2-yl}methyl)-1,3-benzoxazol-2-amine | 452.2326 |
| 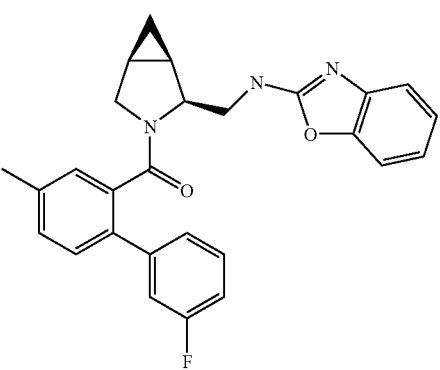 | N-({(1R,2S,5S)-3-[(3'-fluoro-4-methylbiphenyl-2-yl)carbonyl]-3-azabicyclo[3.1.0]hex-2-yl}methyl)-1,3-benzoxazol-2-amine | 442.1916 |

-continued

| Structure | Chemical Name | Found Mass (M + 1) |
|---|---|---|
| 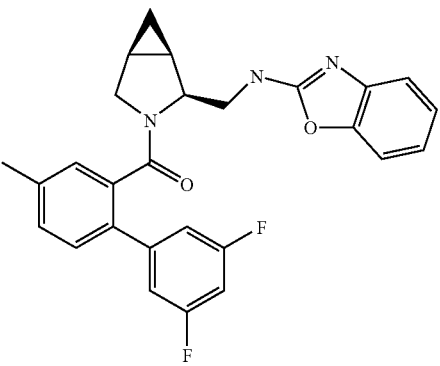 | N-({(1R,2S,5S)-3-[(3',5'-difluoro-4-methylbiphenyl-2-yl)carbonyl]-3-azabicyclo[3.1.0]hex-2-yl}methyl)-1,3-benzoxazol-2-amine | 460.1821 |
| 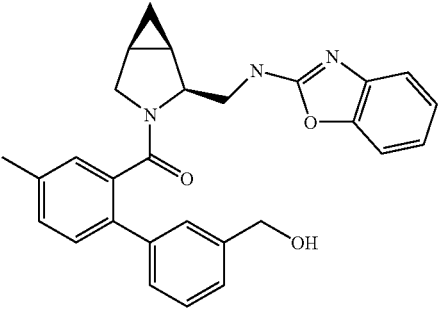 | [2'-({(1R,2S,5S)-2-[(1,3-benzoxazol-2-ylamino)methyl]-3-azabicyclo[3.1.0]hex-3-yl}carbonyl)-4'-methylbiphenyl-3-yl]methanol | 454.2127 |
| 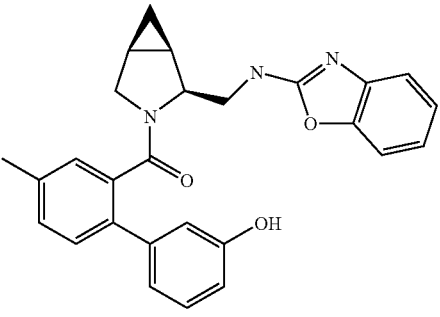 | 2'-({(1R,2S,5S)-2-[(1,3-benzoxazol-2-ylamino)methyl]-3-azabicyclo[3.1.0]hex-3-yl}carbonyl)-4'-methylbiphenyl-3-ol | 440.1958 |
| 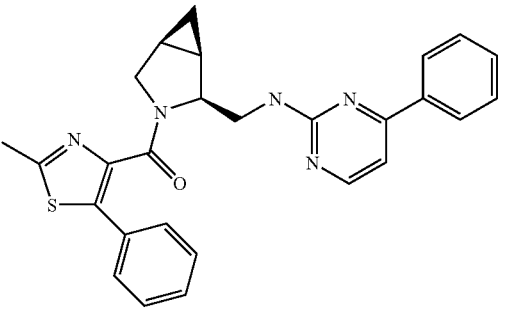 | N-({(1R,2S,5S)-3-[(2-methyl-5-phenyl-1,3-thiazol-4-yl)carbonyl]-3-azabicyclo[3.1.0]hex-2-yl}methyl)-4-phenylpyrimidin-2-amine | 468.1849 |

-continued

| Structure | Chemical Name | Found Mass (M + 1) |
|---|---|---|
| 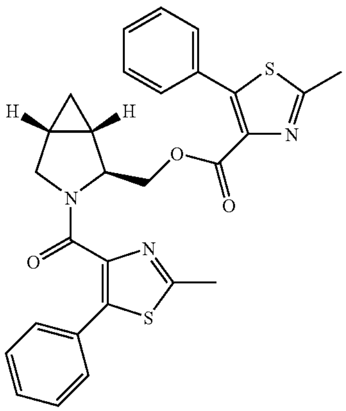 | {(1S,2S,5R)-3-[(2-methyl-5-phenyl-1,3-thiazol-4-yl)carbonyl]-3-azabicyclo[3.1.0]hex-2-yl}methyl 2-methyl-5-phenyl-1,3-thiazole-4-carboxylate | 516.1409 |
| 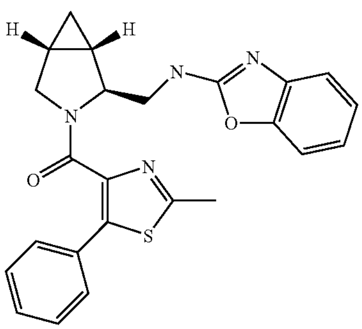 | N-({(1S,2S,5R)-3-[(2-methyl-5-phenyl-1,3-thiazol-4-yl)carbonyl]-3-azabicyclo[3.1.0]hex-2-yl}methyl)-1,3-benzoxazol-2-amine | 431.1527 |
| 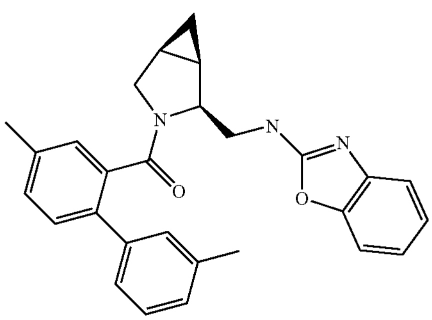 | N-({(1R,2S,5S)-3-[(3',4-dimethylbiphenyl-2-yl)carbonyl]-3-azabicyclo[3.1.0]hex-2-yl}methyl)-1,3-benzoxazol-2-amine | 438.2180 |
| 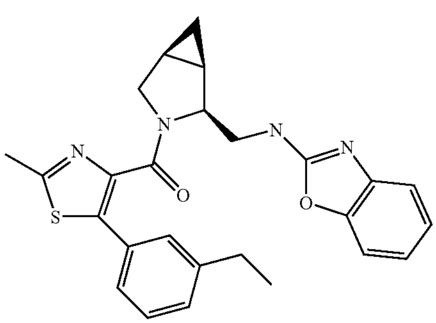 | N-[((1R,2S,5S)-3-{[5-(3-ethylphenyl)-2-methyl-1,3-thiazol-4-yl]carbonyl}-3-azabicyclo[3.1.0]hex-2-yl)methyl]-1,3-benzoxazol-2-amine | 459.1854 |

| Structure | Chemical Name | Found Mass (M + 1) |
|---|---|---|
| 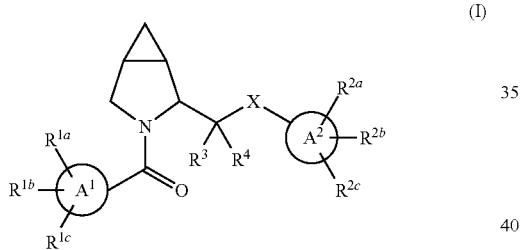 | N-[((1R,2S,5S)-3-{[4-(3-chlorophenyl)-1-methyl-1H-pyrazol-3-yl]carbonyl}-3-azabicyclo[3.1.0]hex-2-yl)methyl]-1,3-benzoxazol-2-amine | 448.1533 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula (I):

(I)

wherein:

$A^1$ is selected from the group consisting of phenyl, napthyl, pyrazolyl, pyridyl, thiazolyl, benzimidazole, N-methyl-benzimidazole, benzthiazole and benzoxazole;

$A^2$ is selected from the group consisting of phenyl, napthyl, pyridyl, benzimidazolyl, benzoxazolyl, benzthiazolyl, pyrimidinyl, thiazolyl, quinazolinyl, quinoxalinyl and quinoxazolinyl;

X is selected from the group consisting of —NH—, —N($C_{1-6}$alkyl)-, —N($C_{1-6}$alkyl)-, —N($C_{3-6}$cycloalkyl)-, —O—, —S—, —S(O)—, —S(O)$_2$—, —CH$_2$—, —CH($C_{1-6}$alkyl)-, and —CH($C_{3-6}$cycloalkyl)-;

$R^{1a}$, $R^{1b}$ and $R^{1c}$ may be absent if the valency of $A^1$ does not permit such substitution and are independently selected from the group consisting of:
(1) hydrogen,
(2) halogen,
(3) hydroxyl,
(4) —(C=O)$_m$—O$_n$—$C_{1-6}$alkyl, and where the alkyl is unsubstituted or substituted with one or more substituents selected from $R^{13}$,
(5) —(C=O)$_m$—O$_n$—$C_{3-6}$cycloalkyl, where the cycloalkyl is unsubstituted or substituted with one or more substituents selected from $R^{13}$,
(6) —(C=O)$_m$—$C_{2-4}$alkenyl, where the alkenyl is unsubstituted or substituted with one or more substituents selected from $R^{13}$,
(7) —(C=O)$_m$—O$_n$-phenyl or —(C=O)$_m$—O$_n$—napthyl, where the phenyl or napthyl is unsubstituted or substituted with one or more substituents selected from $R^{13}$,
(8) —(C=O)$_m$—O$_n$-heterocycle, where the heterocycle is unsubstituted or substituted with one or more substituents selected from $R^{13}$,
(9) —(C=O)$_m$—NR$^{10}$R$^{11}$, wherein $R^{10}$ and $R^{11}$ are independently selected from the group consisting of:
 (a) hydrogen,
 (b) $C_{1-6}$alkyl, which is unsubstituted or substituted with $R^{13}$,
 (c) $C_{3-6}$alkenyl, which is unsubstituted or substituted with $R^{13}$,
 (d) $C_{3-6}$cycloalkyl which is unsubstituted or substituted with $R^{13}$,
 (e) phenyl, which is unsubstituted or substituted with $R^{13}$, and
 (f) heterocycle, which is unsubstituted or substituted with $R^{13}$,
(10) —S(O)$_2$—NR$^{10}$R$^{11}$,
(11) —S(O)$_q$—R$^{12}$, where $R^{12}$ is selected from the definitions of $R^{10}$ and $R^{11}$,
(12) —CO$_2$H,
(13) —CN, and
(14) —NO$_2$;

$R^{2a}$, $R^{2b}$ and $R^{2c}$ may be absent if the valency of $A^2$ does not permit such substitution and are independently selected from the group consisting of:
(1) hydrogen,
(2) halogen,
(3) hydroxyl,
(4) —(C=O)$_m$—O$_n$—$C_{1-6}$alkyl, where the alkyl is unsubstituted or substituted with one or more substituents selected from $R^{13}$,
(5) —(C=O)$_m$—O$_n$—$C_{3-6}$cycloalkyl, where the cycloalkyl is unsubstituted or substituted with one or more substituents selected from $R^{13}$,
(6) —(C=O)$_m$—$C_{2-4}$alkenyl, where the alkenyl is unsubstituted or substituted with one or more substituents selected from $R^{13}$,
(7) —(C=O)$_m$—$C_{2-4}$alkynyl, where the alkynyl is unsubstituted or substituted with one or more substituents selected from $R^{13}$, (8) —(C=O)$_m$—O$_n$-phenyl or —(C=O)$_m$—O$_n$—napthyl, where the phenyl or napthyl is unsubstituted or substituted with one or more substituents selected from R$^{13}$,
(9) —(C=O)$_m$—O$_n$-heterocycle, where the heterocycle is unsubstituted or substituted with one or more substituents selected from R$^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

R$^3$ and R$^4$ are independently selected from the group consisting of:
(1) hydrogen,
(2) halogen,
(3) hydroxyl, and
(4) C$_{1-6}$alkyl, which is unsubstituted or substituted with one or more substituents selected from R$^{13}$,
or R$^3$ and R$^4$ may be joined together to form a C$_{3-6}$cycloalkyl with the carbon atom to which they are attached, where the cycloalkyl is unsubstituted or substituted with one or more substituents selected from R$^{13}$;

R$^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from R$^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from R$^{14}$,
(6) —(C=O)$_m$—C$_{2-4}$alkenyl, where the alkenyl is unsubstituted or substituted with one or more substituents selected from R$^{14}$,
(7) —(C=O)$_m$—C$_{2-4}$alkynyl, where the alkynyl is unsubstituted or substituted with one or more substituents selected from R$^{14}$,
(8) —(C=O)$_m$—O$_n$-phenyl or —(C=O)$_m$—O$_n$—napthyl, where the phenyl or napthyl is unsubstituted or substituted with one or more substituents selected from R$^{14}$,
(9) —(C=O)$_m$—O$_n$-heterocycle, where the heterocycle is unsubstituted or substituted with one or more substituents selected from R$^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;

m is 0 or 1, wherein if m is 0, a bond is present;

n is 0 or 1, wherein if n is 0, a bond is present;

q is 0, 1 or 2;

or a pharmaceutically acceptable salt thereof.

2. The compound of claim 1 of the formula (Ia):

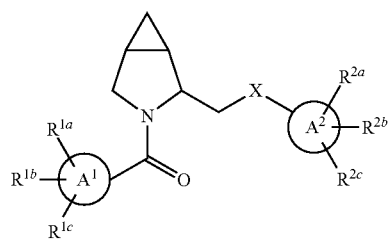

(Ia)

or a pharmaceutically acceptable salt thereof.

3. The compound of claim 1 of the formula (Ib):

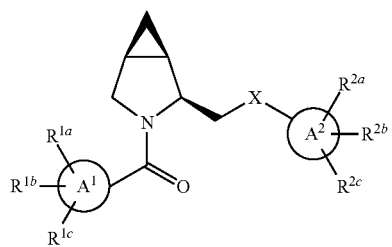

(Ib)

or a pharmaceutically acceptable salt thereof.

4. The compound of claim 1 of the formula (Ic):

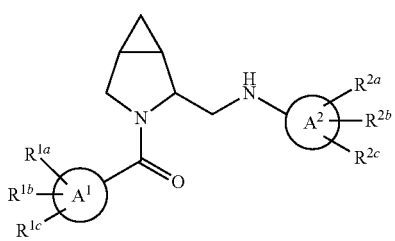

(Ic)

or a pharmaceutically acceptable salt thereof.

5. The compound of claim 1 of the formula (Id):

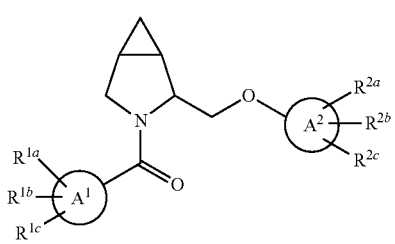

(Id)

or a pharmaceutically acceptable salt thereof.

6. The compound of claim 1 of the formula (Ie):

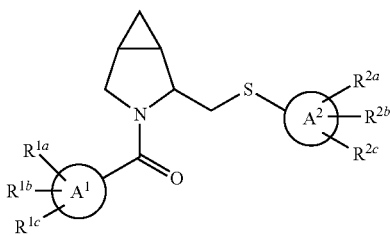

(Ie)

or a pharmaceutically acceptable salt thereof.

7. The compound of claim 1 wherein X is —NH—.

8. The compound of claim 1 wherein X is —O—.

9. The compound of claim 1 wherein X is —S.

10. The compound of claim 1 wherein A1 is selected from the group consisting of phenyl, pyrazolyl, pyridyl, and thiazolyl.

11. The compound of claim 1 wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl, phenyl or napthyl,
(5) —O—$C_{1-6}$alkyl, which is unsubstituted or substituted with halogen, hydroxyl or phenyl,
(6) heteroaryl, wherein heteroaryl is selected from pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —NO$_2$,
(7) phenyl, which is unsubstituted or substituted with halogen, hydroxyl, $C_{1-6}$alkyl, —O—$C_{1-6}$alkyl or —NO$_2$,
(8) —O-phenyl, which is unsubstituted or substituted with halogen, hydroxyl, $C_{1-6}$alkyl, —O—$C_{1-6}$alkyl or —NO$_2$, and
(9) —NH—$C_{1-6}$alkyl, or —N($C_{1-6}$alkyl)($C_{1-6}$alkyl), which is unsubstituted or substituted with halogen, hydroxyl, $C_{1-6}$alkyl, —O—$C_{1-6}$alkyl or —NO$_2$.

12. The compound of claim 11 wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl or napthyl, and
(5) —O—$C_{1-6}$alkyl, which is unsubstituted or substituted with halogen, hydroxyl or phenyl.

13. The compound of claim 12 wherein $R^{1a}$, $R^{1b}$ and $R^{1c}$ are independently selected from the group consisting of:
(1) hydrogen,
(2) halogen, and
(3) $C_{1-6}$alkyl.

14. The compound of claim 1 wherein $A^2$ is selected from the group consisting of: benzimidazolyl, benzoxazolyl, benzthiazolyl, pyrimidinyl, quinazolinyl and quinoxazolinyl.

15. The compound of claim 1 wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl, phenyl or napthyl,
(5) —O—$C_{1-6}$alkyl, which is unsubstituted or substituted with halogen, hydroxyl or phenyl,
(6) heteroaryl, wherein heteroaryl is selected from pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —NO$_2$,
(7) phenyl, which is unsubstituted or substituted with halogen, hydroxyl, $C_{1-6}$alkyl, —O—$C_{1-6}$alkyl or —NO$_2$,
(8) —O-phenyl, which is unsubstituted or substituted with halogen, hydroxyl, $C_{1-6}$alkyl, —O—$C_{1-6}$alkyl or —NO$_2$, and
(9) —NH—$C_{1-6}$alkyl, or —N($C_{1-6}$alkyl)($C_{1-6}$alkyl), which is unsubstituted or substituted with halogen, hydroxyl, $C_{1-6}$alkyl, —O—$C_{1-6}$alkyl or —NO$_2$.

16. The compound of claim 15 wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl, and
(6) —NH—$C_{1-6}$alkyl, or —N($C_{1-6}$alkyl)($C_{1-6}$alkyl), which is unsubstituted or substituted with halogen.

17. The compound of claim 16 wherein $R^{2a}$, $R^{2b}$ and $R^{2c}$ are independently selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen, and
(5) —NH—$C_{1-6}$alkyl, or —N($C_{1-6}$alkyl)($C_{1-6}$alkyl), which is unsubstituted or substituted with halogen.

18. A compound which is selected from the group consisting of:
N-({3-[(2-methyl-5-phenyl-1,3-thiazol-4-yl)carbonyl]-3-azabicyclo[3.1.0]hex-2-yl}methyl)-1,3-benzoxazol-2-amine;
N-methyl-N-({3-[(2-methyl-5-phenyl-1,3-thiazol-4-yl)carbonyl]-3-azabicyclo [3.1.0]hex-2-yl}methyl)-1,3-benzoxazol-2-amine;
N-[(3-{[2-methyl-5-(2-methylphenyl)-1,3-thiazol-4-yl]carbonyl}-3-azabicyclo[3.1.0]hex-2-yl) methyl]-1,3-benzoxazol-2-amine;
N-(1-{3-[(2-methyl-5-phenyl-1,3-thiazol-4-yl)carbonyl]-3-azabicyclo[3 .1.0]hex-2-yl}ethyl)-1,3-benzoxazol-2-amine;
N-({3-[(2-methyl-5-phenyl-1,3-thiazol-4-yl)carbonyl]-3-azabicyclo[3.1.0]hex-2-yl}methyl)-1,3-benzoxazol-2-amine;
2-[({3-[(2-methyl-5-phenyl-1,3-thiazol-4-yl)carbonyl]-3-azabicyclo[3.1.0]hex-2-yl}methyl)thio]-1H-benzimidazole;
2-{[(4-fluorobenzyl)oxy]methyl}-3-[(2-methyl-5-phenyl-1,3-thiazol-4-yl)carbonyl]-3 -azabicyclo[3.1.0] hexane;
[(3-{[4-(3-chlorophenyl)-1-methyl-1H-pyrazol-3-yl]carbonyl}-3-azabicyclo[3.1.0]hexy-2 -yl)methyl]-1,3-benzoxazol-2-amine;
N-({3-[(2-methyl-5-phenyl-1,3-thiazol-4-yl)carbonyl]-3-azabicyclo[3.1.0]hex-2-yl}methyl)-1,3-benzoxazol-2-amine;
N-methyl-N-({3-[(2-methyl-5-phenyl-1,3-thiazol-4-yl)carbonyl]-3-azabicyclo [3.1.0]hex-2 -yl}methyl)-1,3-benzoxazol-2-amine;

2-{[(4-fluorobenzyl)oxy]methyl}-3-[(2-methyl-5-phenyl-1,3-thiazol-4-yl)carbonyl]-3-azabicyclo[3.1.0]hexane;

2-[({3-[(2-methyl-5-phenyl-1,3-thiazol-4-yl)carbonyl]-3-azabicyclo[3.1.0]hex-2-yl}methyl)thio]-1H-benzimidazole;

1-methyl-2-[({3-[(2-methyl-5-phenyl-1,3-thiazol-4-yl)carbonyl]-3-azabicyclo[3.1.0]hex-2-yl}methyl)thio]-1H-benzimidazole;

N-({3-[5-methyl-2-(2H-1,2,3-triazol-2-yl)benzoyl]-3-azabicyclo[3.1.0]hex-2-yl}methyl)-1,3-benzoxazol-2-amine;

N-({3-[2-(2H-1,2,3-triazol-2-yl)benzoyl]-3-azabicyclo[3.1.0]hex-2-yl}methyl)-1,3-benzoxazol-2-amine;

N-methyl-N-({3-[2-(2H-1,2,3-triazol-2-yl)benzoyl]-3-azabicyclo[3.1.0]hex-2-yl}methyl)-1,3-benzoxazol-2-amine;

N-({3-[(2-methyl-5-phenyl-1,3-thiazol-4-yl)carbonyl]-3-azabicyclo[3.1.0]hex-2-yl}methyl)quinoxalin-2-amine;

N-({3-[(2-methyl-5-phenyl-1,3-thiazol-4-yl)carbonyl]-3-azabicyclo[3.1.0]hex-2-yl}methyl)quinazolin-2-amine;

2-[({3-[5-methyl-2-(2H-1,2,3-triazol-2-yl)benzoyl]-3-azabicyclo[3.1.0]hex-2-yl}methyl)thio]-1H-benzimidazole;

1-methyl-2-[({3-]5-methyl-2-(2H-1,2,3-triazol-2-yl)benzoyl]-3-azabicyclo[3.1.0]hex-2-yl}methyl)thio]-1H-benzimidazole;

1-ethyl-2-[({3-[5-methyl-2-(2H-1,2,3-triazol-2-yl)benzoyl]-3-azabicyclo[3.1.0]hex-2-yl}methyl)thio]-1H-benzimidazole;

1-ethyl-2-[({3-[(2-methyl-5-phenyl-1,3-thiazol-4-yl)carbonyl]-3-azabicyclo[3.1.0]hex-2-yl}methyl)thio]-1H-benzimidazole;

N,N-dimethyl-2-{2-[({3-[(2-methyl-5-phenyl-1,3-thiazol-4-yl)carbonyl]-3-azabicyclo[3.1.0]hex-2-yl}methyl)thio]-1H-benzimidazol-1-yl}ethanamine;

1-methyl-N-({3-]5-methyl-2-(2H-1,2,3-triazol-2-yl)benzoyl]-3-azabicyclo[3.1.0]hex-2-yl}methyl)-1H-benzimidazol-2-amine;

1-(methoxymethyl)-2-[({3-[5-methyl-2-(2H-1,2,3-triazol-2-yl)benzoyl]-3-azabicyclo[3.1.0]hex-2-yl}methyl)thio]-1H-benzimidazole;

N-({3-[5-methyl-2-(2H-1,2,3-triazol-2-yl)benzoyl]-3-azabicyclo[3.1.0]hex-2-yl}methyl)quinazolin-2-amine;

N-({3-[5-methyl-2-(2H-1,2,3-triazol-2-yl)benzoyl]-3-azabicyclo[3.1.0]hex-2-yl}methyl)quinoxalin-2-amine;

N-({3-[5-methyl-2-(2H-1,2,3-triazol-2-yl)benzoyl]-3-azabicyclo[3.1.0]hex-2-yl}methyl)-1,3-benzothiazol-2-amine;

1-isopropyl-2-[({3-[5-methyl-2-(2H-1,2,3-triazol-2-yl)benzoyl]-3-azabicyclo[3.1.0]hex-2-yl}methyl)thio]-1H-benzimidazole;

1-methyl-2-[({3-[(1-methyl-4-phenyl-1H-pyrazol-3-yl)carbonyl]-3-azabicyclo[3.1.0]hex-2-yl}methyl)thio]-1H-benzimidazole;

1-methyl-2-[({3-[(3-methyl-1-phenyl-1H-pyrazol-5-yl)carbonyl]-3-azabicyclo[3.1.0]hex-2-yl}methyl)thio]-1H-benzimidazole;

N-({3-[(3-phenylpyridin-2-yl)carbonyl]-3-azabicyclo[3.1.0]hex-2-yl}methyl)-1,3-benzoxazol-2-amine;

N-({3-[(1-methyl-4-phenyl-1H-pyrazol-3-yl)carbonyl]-3-azabicyclo[3.1.0]hex-2-yl}methyl)-1,3-benzoxazol-2-amine;

N-({3-[(1-methyl-4-phenyl-1H-pyrazol-3-yl)carbonyl]-3-azabicyclo[3.1.0]hex-2-yl}methyl)quinoxalin-2-amine;

6,7-difluoro-N-({3-[5-methyl-2-(2H-1,2,3-triazol-2-yl)benzoyl]-3-azabicyclo[3.1.0]hex-2-yl}methyl)quinoxalin-2-amine;

5-chloro-N-({3-]5-methyl-2-(2H-1,2,3-triazol-2-yl)benzoyl]-3-azabicyclo[3.1.0]hex-2-yl}methyl)-1,3-benzoxazol-2-amine;

N-({3-[5-methyl-2-(2H-1,2,3-triazol-2-yl)benzoyl]-3-azabicyclo[3.1.0]hex-2-yl}methyl)[1,3]oxazolo[5,4-b]pyridin-2-amine;

N-({3-[5-methyl-2-(2H-1,2,3-triazol-2-yl)benzoyl]-3-azabicyclo[3.1.0]hex-2-yl}methyl)[1,3]oxazolo[4,5-b]pyridin-2-amine;

N-{[3-(3,3'-bipyridin-2-ylcarbonyl)-3-azabicyclo[3.1.0]hex-2-yl]methyl}-1,3-benzoxazol-2-amine;

2-[({3-[5-methyl-2-(2H-1,2,3-triazol-2-yl)benzoyl]-3-azabicyclo[3.1.0]hex-2-yl}methyl)thio]-9H-purine;

2-[({3-[5-methyl-2-(2H-1,2,3-triazol-2-yl)benzoyl]-3-azabicyclo[3.1.0]hex-2-yl}methyl)thio]quinazolin-4(3H)-one;

1-(2-fluoroethyl)-5-methyl-2-[({3-[5-methyl-2-(2H-1,2,3-triazol-2-yl)benzoyl]-3-azabicyclo[3.1.0]hex-2-yl}methyl)thio]-1H-benzimidazole;

N-[(3-{[3-(3-methoxyphenyl)pyridin-2-yl]carbonyl}-3-azabicyclo[3.1.0]hex-2-yl)methyl]-1,3-benzoxazol-2-amine;

N-[(3-{[3-(4-fluorophenyl)pyridin-2-yl]carbonyl}-3-azabicyclo[3.1.0]hex-2-yl)methyl]-1,3-benzoxazol-2-amine;

N-[(3-{[3-(3,5-dimethyl-1H-pyrazol-4-yl)pyridin-2-yl]carbonyl}-3-azabicyclo[3.1.0]hex-2-yl)methyl]-1,3-benzoxazol-2-amine;

N-({3-]5-methyl-2-(1-methyl-1H-imidazol-2-yl)benzoyl]-3-azabicyclo[3.1.0]hex-2-yl}methyl)-1,3-benzoxazol-2-amine;

N-({3-[5-methyl-2-(1,3-thiazol-4-yl)benzoyl]-3-azabicyclo[3.1.0]hex-2-yl}methyl)-1,3-benzoxazol-2-amine;

N-({3-[2-(2-methoxypyrimidin-5-yl)-5-methylbenzoyl]-3-azabicyclo[3.1.0]hex-2-yl}methyl)-1,3-benzoxazol-2-amine;

N-({3-[2-(6-methoxypyridin-3-yl)-5-methylbenzoyl]-3-azabicyclo[3.1.0]hex-2-yl}methyl)-1,3-benzoxazol-2-amine;

N-({3-[2-(2-ethoxy-1,3-thiazol-4-yl)-5-methylbenzoyl]-3-azabicyclo[3.1.0]hex-2-yl}methyl)-1,3-benzoxazol-2-amine;

N-{[3-(5-methyl-2-pyridazin-3-ylbenzoyl)-3-azabicyclo[3.1.0]hex-2-yl]methyl}-1,3-benzoxazol-2-amine;

N-({3-[(4-methylbiphenyl-2-yl)carbonyl]-3-azabicyclo[3.1.0]hex-2-yl}methyl)-1,3-benzoxazol-2-amine;

N-{[3-(5-methyl-2-pyridin-3-ylbenzoyl)-3-azabicyclo[3.1.0]hex-2-yl]methyl}-1,3-benzoxazol-2-amine;

N-(1-{3-[(2-methyl-5-phenyl-1,3-thiazol-4-yl)carbonyl]-3-azabicyclo[3.1.0]hex-2-yl}ethyl)-1,3-benzoxazol-2-amine;

N-{[3-({3-[3-(trifluoromethoxy)phenyl]pyridin-2-yl}carbonyl)-3-azabicyclo[3.1.0]hex-2-yl]methyl}-1,3-benzoxazol-2-amine;

N-{[3-({3-[3-(dimethylamino)phenyl]pyridin-2-yl}carbonyl)-3-azabicyclo[3.1.0]hex-2-yl]methyl}-1,3-benzoxazol-2-amine;

N-[(3-{[3-(3-chlorophenyl)pyridin-2-yl]carbonyl}-3-azabicyclo[3.1.0]hex-2-yl)methyl]-1,3-benzoxazol-2-amine;

N-[(3-{[3-(3-methylphenyl)pyridin-2-yl]carbonyl}-3-azabicyclo[3.1.0]hex-2-yl)methyl]-1,3-benzoxazol-2-amine;

N-({3-[(3'-methoxy-4-methylbiphenyl-2-yl)carbonyl]-3-azabicyclo[3.1.0]hex-2-yl}methyl)-1,3-benzoxazol-2-amine;

N-[(3-{[5-(3-methoxyphenyl)-2-methyl-1,3-thiazol-4-yl]carbonyl}-3-azabicyclo[3.1.0]hex-2-yl)methyl]-1,3-benzoxazol-2-amine;

N-[(3-{[2-methyl-5-(3-methylphenyl)-1,3-thiazol-4-yl]carbonyl}-3-azabicyclo[3.1.0]hex-2-yl)methyl]-1,3-benzoxazol-2-amine;

N-[(3-{[5-(3-chlorophenyl)-2-methyl-1,3-thiazol-4-yl]carbonyl}-3-azabicyclo[3.1.0]hex-2-yl)methyl]-1,3-benzoxazol-2-amine;

N-[(3-{[5-(3-fluorophenyl)-2-methyl-1,3-thiazol-4-yl]carbonyl}-3-azabicyclo[3.1.0]hex-2-yl)methyl]-1,3-benzoxazol-2-amine;

N-{[3-({2-methyl-5-[3-(trifluoromethoxy)phenyl]-1,3-thiazol-4-yl}carbonyl)-3-azabicyclo[3.1.0]hex-2-yl]methyl}-1,3-benzoxazol-2-amine;

N-[(3-{[2-methyl-5-(2-methylphenyl)-1,3-thiazol-4-yl]carbonyl}-3-azabicyclo[3.1.0]hex-2-yl)methyl]-1,3-benzoxazol-2-amine;

N-[(3-{[2-methyl-5-(4-methylphenyl)-1,3-thiazol-4-yl]carbonyl}-3-azabicyclo[3.1.0]hex-2-yl)methyl]-1,3-benzoxazol-2-amine;

N-({3-[5-methyl-2-(1,3-thiazol-2-yl)benzoyl]-3-azabicyclo[3.1.0]hex-2-yl}methyl)-1,3-benzoxazol-2-amine;

N-({3-[5-methyl-2-(1,3-thiazol-5-yl)benzoyl]-3-azabicyclo[3.1.0]hex-2-yl}methyl)-1,3-benzoxazol-2-amine;

N-({3-[(2'-methoxy-4-methylbiphenyl-2-yl)carbonyl]-3-azabicyclo[3.1.0]hex-2-yl}methyl)-1,3-benzoxazol-2-amine;

N-({3-[(4'-methoxy-4-methylbiphenyl-2-yl)carbonyl]-3-azabicyclo[3.1.0]hex-2-yl}methyl)-1,3-benzoxazol-2-amine;

N-({3-[(3',4',5'-trimethylbiphenyl-2-yl)carbonyl]-3-azabicyclo[3.1.0]hex-2-yl}methyl)-1,3-benzoxazol-2-amine;

N-({3-[(3'-fluoro-4-methylbiphenyl-2-yl)carbonyl]-3-azabicyclo[3.1.0]hex-2-yl}methyl)-1,3-benzoxazol-2-amine;

N-({3-[(3',5'-difluoro-4-methylbiphenyl-2-yl)carbonyl]-3-azabicyclo [3.1.0]hex-2-yl}methyl)-1,3-benzoxazol-2-amine;

[2'-({2-[(1,3-benzoxazol-2-ylamino)methyl]-3-azabicyclo[3.1.0]hex-3-yl}carbonyl)-4'-methylbiphenyl-3-yl]methanol;

2'-({2-[(1,3-benzoxazol-2-ylamino)methyl]-3-azabicyclo [3.1.0]hex-3-yl}carbonyl)-4'-methylbiphenyl-3-ol;

N-({3-[(2-methyl-5-phenyl-1,3-thiazol-4-yl)carbonyl]-3-azabicyclo[3.1.0]hex-2-yl}methyl)-4-phenylpyrimidin-2-amine;

{3-[(2-methyl-5-phenyl-1,3-thiazol-4-yl)carbonyl]-3-azabicyclo[3.1.0]hex-2-yl}methyl 2-methyl-5-phenyl-1,3-thiazole-4-carboxylate;

N-({3-[(2-methyl-5-phenyl-1,3-thiazol-4-yl)carbonyl]-3-azabicyclo[3.1.0]hex-2-yl}methyl)-1,3-benzoxazol-2-amine;

N-({3-[(3',4-dimethylbiphenyl-2-yl)carbonyl]-3-azabicyclo[3.1.0]hex-2-yl}methyl)-1,3-benzoxazol-2-amine;

N-[(3-{[5-(3-ethylphenyl)-2-methyl-1,3-thiazol-4-yl]carbonyl}-3-azabicyclo[3.1.0]hex-2-yl)methyl]-1,3-benzoxazol-2-amine; and N-[((1R,2S,5S)-3-{[4-(3-chlorophenyl)-1-methyl-1H-pyrazol-3-yl]carbonyl}-3-azabicyclo[3.1.0]hex-2-yl)methyl]-1,3-benzoxazol-2-amine;

or a pharmaceutically acceptable salt thereof.

19. A pharmaceutical composition which comprises an inert carrier and a compound of claim 1 or a pharmaceutically acceptable salt thereof.

20. A method for enhancing the quality of sleep in a mammalian patient in need thereof which comprises administering to the patient a therapeutically effective amount of the compound of claim 1 or a pharmaceutically acceptable salt thereof.

21. A method for treating insomnia in a mammalian patient in need thereof which comprises administering to the patient a therapeutically effective amount of the compound of claim 1 or a pharmaceutically acceptable salt thereof.

* * * * *